United States Patent
Hauswirth et al.

(10) Patent No.: US 10,533,187 B2
(45) Date of Patent: Jan. 14, 2020

(54) METHODS AND COMPOSITIONS FOR RESTORATION OF CONE FUNCTION IN BCM

(71) Applicant: University of Florida Research Foundation, Incorporated, Gainesville, FL (US)

(72) Inventors: William W. Hauswirth, Gainesville, FL (US); Ji-Jing Pang, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 159 days.

(21) Appl. No.: 15/559,315

(22) PCT Filed: Mar. 18, 2016

(86) PCT No.: PCT/US2016/023252
§ 371 (c)(1),
(2) Date: Sep. 18, 2017

(87) PCT Pub. No.: WO2016/149664
PCT Pub. Date: Sep. 22, 2016

(65) Prior Publication Data
US 2018/0112231 A1    Apr. 26, 2018

Related U.S. Application Data

(60) Provisional application No. 62/134,822, filed on Mar. 18, 2015.

(51) Int. Cl.
| | |
|---|---|
| *A61K 48/00* | (2006.01) |
| *A61P 27/02* | (2006.01) |
| *C12N 15/00* | (2006.01) |
| *C12N 15/63* | (2006.01) |
| *C12N 15/79* | (2006.01) |
| *C12N 15/85* | (2006.01) |
| *C12N 15/86* | (2006.01) |
| *A61K 9/00* | (2006.01) |
| *A61K 38/17* | (2006.01) |
| *C07K 14/72* | (2006.01) |

(52) U.S. Cl.
CPC ............ *C12N 15/86* (2013.01); *A61K 9/0048* (2013.01); *A61K 38/177* (2013.01); *A61K 48/0058* (2013.01); *A61K 48/0075* (2013.01); *A61P 27/02* (2018.01); *C07K 14/723* (2013.01); *C12N 15/85* (2013.01); *C12N 2750/14143* (2013.01); *C12N 2750/14171* (2013.01); *C12N 2830/008* (2013.01); *C12N 2830/50* (2013.01)

(58) Field of Classification Search
CPC .. A61K 38/177; A61K 38/1709; A61K 48/00; A61K 48/005; A61K 48/0058; A61K 48/0075; A61P 27/02; C07K 14/723; C12N 15/00; C12N 15/63; C12N 15/79; C12N 15/85; C12N 15/86; C12N 15/8645; C12N 2750/14141; C12N 2750/14143; C12N 2830/00; C12N 2830/008; C12N 2830/50
See application file for complete search history.

(56) References Cited

U.S. PATENT DOCUMENTS

| | | | |
|---|---|---|---|
| 9,198,595 B2* | 12/2015 | Neitz | A61B 5/0496 |
| 2012/0172419 A1* | 7/2012 | Neitz | A61B 5/0496 514/44 R |
| 2013/0259833 A1 | 10/2013 | Pan | |
| 2014/0080900 A1* | 3/2014 | Neitz | A61B 5/0496 514/44 R |
| 2014/0364486 A1* | 12/2014 | Ye | A61K 48/00 514/44 R |

FOREIGN PATENT DOCUMENTS

WO    WO 11/034947    *    3/2011

OTHER PUBLICATIONS

Alexander et al, Nature Medicine 13(6): 685-687, 2007.*
Michaelides et al, Eye 19: 2-10, 2005.*
Zhang et al, Invest. Ophth. & Vis. Sci. 42: p. 1403, abstract only, Apr. 2011.*
Huang et al, Mol. Vision 19: 1422-1432, 2013.*
Matalon et al, Mol. Therapy 7(5): 580-587, 2003.*
International Search Report and Written Opinion for Application No. PCT/US2016/023252 dated Jul. 13, 2016.
International Preliminary Report on Patentability for Application No. PCT/US2016/023252 dated Sep. 28, 2017.
Azzoni et al., The impact of polyadenylation signals on plasmid nuclease-resistance and transgene expression. Journal of Gene Medicine. Apr. 2007;9(5):392-402.
Daniele et al., A mouse M-opsin monochromat: Retinal cone photoreceptors have increased M-opsin expression when S-opsin is knocked out. Vision Research. 2011;51(4):447-58.
Mancuso et al., Gene therapy for red-green colour blindness in adult primates. Nature. Oct. 8, 2009;461(7265):784-787. Author manuscript.

* cited by examiner

*Primary Examiner* — Kevin K Hill
(74) *Attorney, Agent, or Firm* — Wolf, Greenfield & Sacks, P.C.

(57) ABSTRACT

Provided are nucleic acid sequences, recombinant adeno-associated viral particles, compositions, and methods related to treating cone monochromacies, such as blue cone monochromacy (BCM). Specifically, the nucleic acid sequences, recombinant adeno-associated viral particles, compositions, and methods involve use of an M-opsin gene operably linked to a cone-specific promoter. Further disclosed is the sequence of a cone-specific PR2.1 promoter.

18 Claims, 6 Drawing Sheets
Specification includes a Sequence Listing.

Feature Map:

| | | |
|---|---|---|
| ITR 5' | Start: 1 | End: 143 |
| PR 2.1 (promoter) | Start: 163 | End: 2271 |
| mOpsin1mv (cone opsin) | Start: 2478 | End: 3561 |
| SV40 Poly(A) | Start: 3569 | End: 3767 |
| bGH Poly(A) | Start: 3784 | End: 4006 |
| ITR 3' | Start: 4019 | End: 4161 |
| ColE1 ori | Start: 4607 | End: 4832 |
| AMP(R) | Start: 5082 | End: 6082 |
| f1(+) origin | Start: 6486 | End: 6945 |

```
TTGGCCACTCCCTCTCTGCGCGCTCGCTCGCTCACTGAGGCCGGGCGACCAAAGGTCGCCCGACGCCCGGGCTTTTGCCC
GGGCGGCCTCAGTGAGCGAGCGAGCGCGCAGAGAGGGAGTGGCCAACTCCATCACTAGGGGTTCCTAGATCTGAATTCG
GTACCCCCGGGGGATCCTCTAGAGTCGACAGGCCTACAGCAGCCAGGGTGAGATTATGAGGCTGAGCTGAGAATATCAA
GACTGTACCGAGTAGGGGGCCTTGGCAAGTGTGGAGAGCCCGGCAGCTGGGGCAGAGGGCGGAGTACGGTGTGCGTTTA
CGGACCTCTTCAAACGAGGTAGGAAGGTCAGAAGTCAAAAAGGGAACAAATGATGTTTAACCACACAAAAAATGAAAATC
CAATGGTTGGATATCCATTCCAAATACACAAAGGCAACGGATAAGTGATCCGGGCCAGGCACAGAAGGCCATGCACCCG
TAGGATTGCACTCAGAGCTCCCAAATGCATAGGAATAGAAGGGTGGGTGCAGGAGGCTGAGGGGTGGGAAAGGGCATG
GGTGTTTCATGAGGACAGAGCTTCCGTTTCATGCAATGAAAAGAGTTTGGAGACGGATGGTGGTGACTGGACTATACAC
TTACACACGGTAGCGATGGTACACTTTGTATTATGTATATTTTACCACGATCTTTTTAAAGTGTCAAAGGCAAATGGCC
AAATGGTTCCTTGTCCTATAGCTGTAGCAGCCATCGGCTGTTAGTGACAAAGCCCCTGAGTCAAGATGACAGCAGCCCC
CATAACTCCTAATCGGCTCTCCCGCGTGGAGTCATTTAGGAGTAGTCGCATTAGAGACAAGTCCAACATCTAATCTTCC
ACCCTGCCAGGGCCCCAGCTGGCAGCGAGGGTGGGAGACTCCGGGCAGAGCAGAGGGCGCTGACATTGGGGCCCGGCCT
GGCTTGGGTCCCTCTGGCCTTTCCCCAGGGGCCCTCTTTCCTTGGGGCTTTCTTGGGCCGCCACTGCTCCCGCTCCTCT
CCCCCCATCCCACCCCCTCACCCCCTCGTTCTTCATATCCTTCTCTAGTGCTCCCTCCACTTTCATCCACCCTTCTGCA
AGAGTGTGGGACCACAAATGAGTTTTCACCTGGCCTGGGGACACACGTGCCCCCACAGGTGCTGAGTGACTTTCTAGGA
CAGTAATCTGCTTTAGGCTAAAATGGGACTTGATCTTCTGTTAGCCCTAATCATCAATTAGCAGAGCCGGTGAAGGTGC
AGAACCTACCGCCTTTCCAGGCCTCCTCCCACCTCTGCCACCTCCACTCTCCTTCCTGGGATGTGGGGGCTGGCACACG
TGTGGCCCAGGGCATTGGTGGGATTGCACTGAGCTGGGTCATTAGCGTAATCCTGGACAAGGGCAGACAGGGCGAGCGG
AGGGCCAGCTCCGGGGCTCAGGCAAGGCTGGGGGCTTCCCCAGACACCCCACTCCTCCTCTGCTGGACCCCCACTTCA
TAGGGCACTTCGTGTTCTCAAAGGGCTTCCAAATAGCATGGTGGCCTTGGATGCCCAGGGAAGCCTCAGAGTTGCTTAT
CTCCCTCTAGACAGAAGGGGAATCTCGGTCAAGAGGGAGAGGTCGCCCTGTTCAAGGCCACCCAGCCAGCTCATGGCGG
TAATGGGACAAGGCTGGCCAGCCATCCCACCCTCAGAAGGGACCCGGTGGGGCAGGTGATCTCAGAGGAGGCTCACTTC
TGGGTCTCACATTCTTGGATCCGGTTCCAGGCCTCGGCCCTAAATAGTCTCCCTGGGCTTTCAAGAGAACCACATGAGA
AAGGAGGATTCGGGCTCTGAGCAGTTTCACCACCCACCCCCCAGTCTGCAAATCCTGACCCGAGGGTCCACCTGCCCCA
AAGGCGGACGCAGGACAGTAGAAGGGAACAGAGAACACATAAACACAGAGAGGGCCACAGCGGCTCCCACAGTCACCGC
CACCTTCCTGGCGGGATGGGTGGGGCGTCTGAGTTTGGTTCCCAGCAAATCCCTCTGAGCCGCCCTTGCGGGCTCGCC
TCAGGAGCAGGGGAGCAAGAGGTGGAGGAGGAGGTCTAAGTCCCAGGCCCAATTAAGAGATCAGGTAGTGTAGGGTTT
GGGAGCTTTTAAGGTGAAGAGGCCCGGGCTGATCCCACAGGCCAGTATAAAGCGCCGTGACCCTCAGGTGATGCGCCAG
GGCCGGCTGCCTGCGGGGACAGGGCTTTCCATAGCCATGAGGATCCGAATTCGGATCCCCATGTCTAGAGGATCCGGTA
CTCGAGGAACTGAAAAACCAGAAAGTTAACTGGTAAGTTTAGTCTTTTTGTCTTTTATTTCAGGTCCCGGATCCGGTGG
TGGTGCAAATCAAAGAACTGCTCCTCAGTGGATGTTGCCTTTACTTCTAGGCCTGTACGGAAGTGTTACTTCTGCTCTA
AAAGCTGCGGAATTGTACCCGCGGCCGCCACCATGGCCCAAAGGCTTACAGGTGAACAGACACTGGACCACTATGAGGA
TAGCACCCATGCAAGCATCTTCACCTATACCAACAGCAACAGCACCAAAGGTCCCTTTGAAGGCCCCAATTATCACATT
```

METHODS AND COMPOSITIONS FOR RESTORATION OF CONE FUNCTION IN BCM

RELATED APPLICATIONS

This application claims priority under 35 U.S.C. § 119(e) to U.S. provisional application No. 62/134,822, filed Mar. 18, 2015, the content of which is incorporated herein by reference in its entirety.

BACKGROUND

Human photoreceptors have three kinds of cones to distinguish among red, green and blue colors. Blue Cone Monochromacy (BCM) patients lack functional long wavelength-sensitive and medium wavelength-sensitive cones in the retina required for detection of red and green colors, which leaves the patients legally blind. There is currently no treatment for BCM.

SUMMARY

Aspects of the disclosure relate to nucleic acids, recombinant adeno-associated virus (rAAV) particles, compositions, and methods related to gene therapy for cone monochromacy and other eye disorders such as protanopia and deuteranopia.

As described herein, an M-opsin gene driven by the cone-specific promoter PR2.1 was delivered to the eye of a mouse model of BCM using rAAV particles. It was found that eyes treated with the rAAV particles were able to express the M-opsin gene in cone cells and that M-opsin function was restored in the treated eyes. As disclosed herein, such expression vectors and rAAV particles are useful for treatment of cone monochromacy and other eye disorders such as protanopia and deuteranopia, including in humans.

In some aspects, the disclosure provides a nucleic acid comprising an expression construct containing an M-opsin gene operably linked to a cone-specific promoter, wherein the expression construct is flanked by inverted terminal repeat (ITR) sequences (e.g., an ITR sequence at each end of the expression construct). In some embodiments, the ITR sequence is an AAV2 ITR sequence. In some embodiments, the cone-specific promoter is a PR2.1 promoter having the sequence of SEQ ID NO: 1. In some embodiments, the expression construct further contains nucleic acid segments that encode an SV40 polyadenylation signal and a bovine growth hormone polyadenylation signal, wherein the nucleic acid segments are positioned 3' to the M-opsin gene. In some embodiments, the nucleic acid comprises or consists of the sequence of SEQ ID NO: 2. In some embodiments, the nucleic acid is a recombinant adeno-associated virus (rAAV) vector. In some embodiments, the nucleic acid is a plasmid, e.g., containing one or more of an origin of replication and a resistance marker.

Other aspects of the disclosure relate to a recombinant adeno-associated virus (rAAV) particle comprising the nucleic acid of any one of the above embodiments or as otherwise described herein. In some embodiments, the rAAV particle is an AAV5 particle (e.g., a particle that has AAV5 capsid proteins).

Yet other aspects of the disclosure relate to a composition comprising a plurality of the rAAV particle of any one of the above embodiments or as otherwise described herein. In some embodiments, the composition further comprises a pharmaceutically acceptable carrier.

Other aspects of the disclosure relate to a method of treating a cone monochromacy, protanopia, or deuteranopia in a subject, the method comprising administering a therapeutically effective amount of the rAAV particle of any one of the above embodiments or as otherwise described herein or the composition of any one of the above embodiments or as otherwise described herein to a subject having a cone monochromacy, protanopia, or deuteranopia. In some embodiments, the rAAV particle or composition are administered via subretinal injection. In some embodiments, the subject has blue cone monochromacy. In some embodiments, the subject is a human subject.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 1B shows the sequence of the exemplary plasmid. The sequence corresponds to SEQ ID NO: 2.

DETAILED DESCRIPTION

Figure 1A:
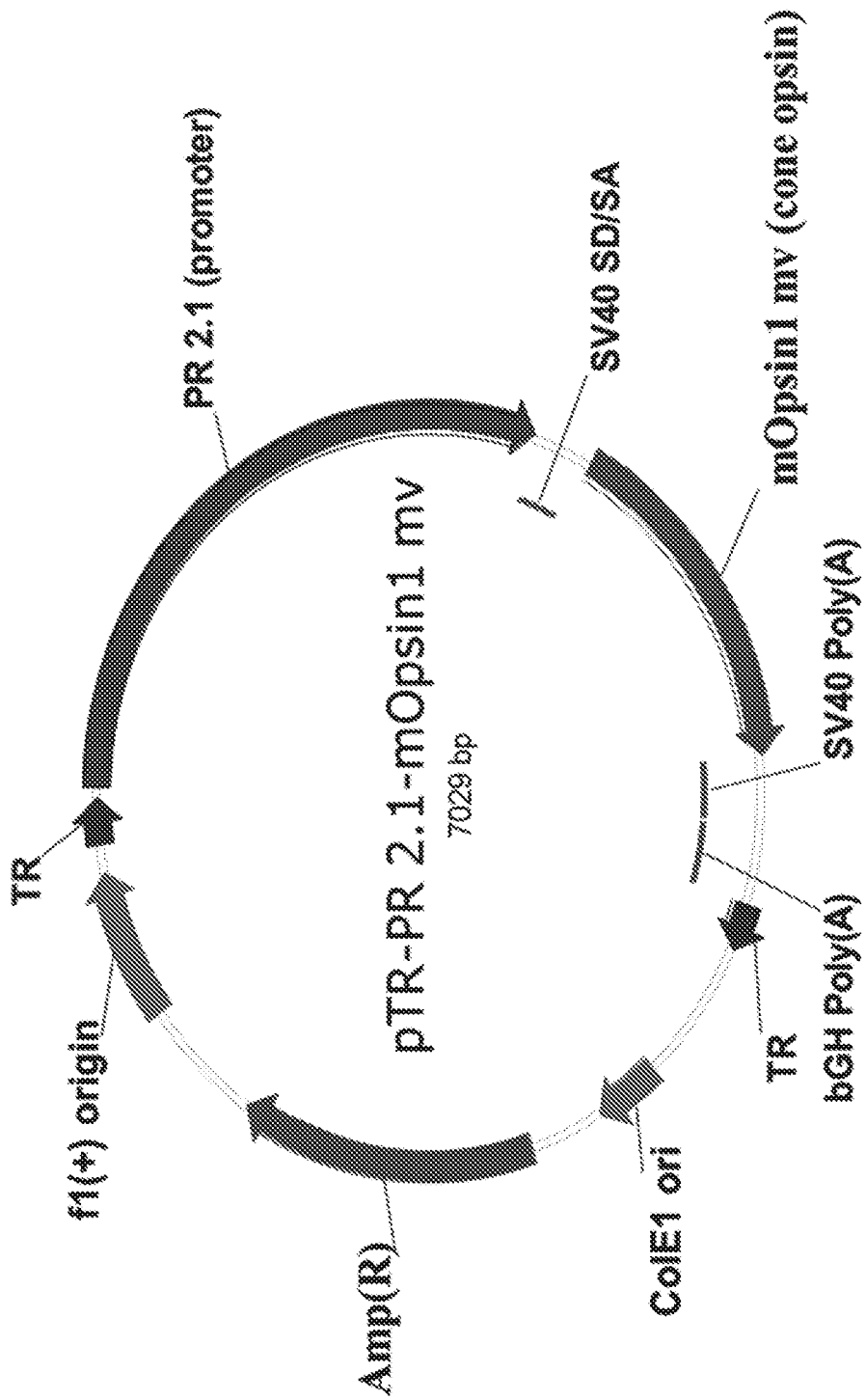
FIG. 1A is a schematic drawing of the exemplary plasmid containing the exemplary construct that was packaged into AAV5 in Example 1.

Aspects of the disclosure relate to nucleic acids, recombinant AAV (rAAV) particles and nucleic acids, compositions, and methods of treating an ocular disorder, such as blue cone monochromacy (BCM).

In some embodiments, a nucleic acid is provided, the nucleic acid comprising an expression construct containing an opsin gene (e.g., an M-opsin gene) operably linked to a promoter. In some embodiments, promoters suitable for use with the methods and compositions described herein include constitutive promoters, strong promoters (e.g., CMV promoters), inducible promoters, and tissue-specific or cell-specific promoters (e.g., promoters that preferentially facilitate expression in a limited number of tissues or cell types). In some embodiments, tissue-specific or cell-specific promoters include eye-specific promoters (e.g., cone-specific promoters, rod-specific promoters, retina-specific promoters, retinal cell-specific promoters, photoreceptor cell-specific promoters, and the like). In some embodiments, the promoter is an mGluR6 promoter, a GNA01 promoter, a CBA/smCBA (fusion of the CMV immediate early enhancer and bovine beta actin promoter plus intro 1-exon1 junction) promoter, CBA promoter (chicken beta actin), CMV promoter, RSV promoter, SV40 promoter, MoMLV promoter, or derivatives, mutants and/or fragments thereof. Other promoters that may similarly be utilized within the context of the present invention include cell or tissue specific promoters (e.g., a rod, cone, or ganglia derived promoter), or inducible promoters. Representative examples of suitable inducible promoters include inducible promoters sensitive to an antibiotic, e.g., tetracycline-responsive promoters such as "tet-on" and/or "tet-off" promoters. Inducible promoters may also include promoters sensitive to chemicals other than antibiotics.

In some embodiments, a nucleic acid is provided, the nucleic acid comprising an expression construct containing an opsin gene (e.g., an M-opsin gene) operably linked to a cone-specific promoter. Exemplary, non-limiting cone-specific promoters include PR2.1, red/green opsin promoter, IRBPe/GNAT2 promoter, and synGNAT2/GNAT2 (see, e.g., Dyka et al. Cone specific promoter for use in gene therapy of retinal degenerative diseases. Adv Exp Med Biol. 2014; 801:695-701 and U.S. Patent Application Publication No. US20140275231). In some embodiments, the expression construct is flanked on each side by an inverted terminal repeat sequence. In some embodiments, the cone-specific promoter is a PR2.1 promoter having the sequence of SEQ ID NO: 1.

```
PR2.1 promoter sequence:
                                        (SEQ ID NO: 1)
CCCCGGGGGATCCTCTAGAGTCGACAGGCCTACAGCAGCCAGGGTGAGAT

TATGAGGCTGAGCTGAGAATATCAAGACTGTACCGAGTAGGGGCCTTGG

CAAGTGTGGAGAGCCCGGCAGCTGGGGCAGAGGGCGGAGTACGGTGTGCG

TTTACGGACCTCTTCAAACGAGGTAGGAAGGTCAGAAGTCAAAAAGGGAA

CAAATGATGTTTAACCACACAAAAATGAAAATCCAATGGTTGGATATCCA

TTCCAAATACACAAAGGCAACGGATAAGTGATCCGGGCCAGGCACAGAAG

GCCATGCACCCGTAGGATTGCACTCAGAGCTCCCAAATGCATAGGAATAG

AAGGGTGGGTGCAGGAGGCTGAGGGGTGGGGAAAGGGCATGGGTGTTTCA

TGAGGACAGAGCTTCCGTTTCATGCAATGAAAAGAGTTTGGAGACGGATG

GTGGTGACTGGACTATACACTTACACACGGTAGCGATGGTACACTTTGTA

TTATGTATATTTTACCACGATCTTTTTAAAGTGTCAAAGGCAAATGGCCA

AATGGTTCCTTGTCCTATAGCTGTAGCAGCCATCGGCTGTTAGTGACAAA

GCCCCTGAGTCAAGATGACAGCAGCCCCCATAACTCCTAATCGGCTCTCC

CGCGTGGAGTCATTTAGGAGTAGTCGCATTAGAGACAAGTCCAACATCTA

ATCTTCCACCCTGCCAGGGCCCCAGCTGGCAGCGAGGGTGGGAGACTCCG

GGCAGAGCAGAGGGCGCTGACATTGGGGCCCGGCCTGGCTTGGGTCCCTC

TGGCCTTTCCCCAGGGGCCCTCTTTCCTTGGGGCTTTCTTGGGCCGCCAC

TGCTCCCGCTCCTCTCCCCCCATCCCACCCCCTCACCCCCTCGTTCTTCA

TATCCTTCTCTAGTGCTCCCTCCACTTTCATCCACCCTTCTGCAAGAGTG

TGGGACCACAAATGAGTTTTCACCTGGCCTGGGGACACACGTGCCCCCAC

AGGTGCTGAGTGACTTTCTAGGACAGTAATCTGCTTTAGGCTAAAATGGG

ACTTGATCTTCTGTTAGCCCTAATCATCAATTAGCAGAGCCGGTGAAGGT

-continued
GCAGAACCTACCGCCTTTCCAGGCCTCCTCCCACCTCTGCCACCTCCACT

CTCCTTCCTGGGATGTGGGGGCTGGCACACGTGTGGCCCAGGGCATTGGT

GGGATTGCACTGAGCTGGGTCATTAGCGTAATCCTGGACAAGGGCAGACA

GGGCGAGCGGAGGGCCAGCTCCGGGGCTCAGGCAAGGCTGGGGGCTTCCC

CCAGACACCCCACTCCTCCTCTGCTGGACCCCCACTTCATAGGGCACTTC

GTGTTCTCAAAGGGCTTCCAAATAGCATGGTGGCCTTGGATGCCCAGGGA

AGCCTCAGAGTTGCTTATCTCCCTCTAGACAGAAGGGGAATCTCGGTCAA

GAGGGAGAGGTCGCCCTGTTCAAGGCCACCCAGCCAGCTCATGGCGGTAA

TGGGACAAGGCTGGCCAGCCATCCCACCCTCAGAAGGGACCCGGTGGGGC

AGGTGATCTCAGAGGAGGCTCACTTCTGGGTCTCACATTCTTGGATCCGG

TTCCAGGCCTCGGCCCTAAATAGTCTCCCTGGGCTTTCAAGAGAACCACA

TGAGAAAGGAGGATTCGGGCTCTGAGCAGTTTCACCACCCACCCCCCAGT

CTGCAAATCCTGACCCGAGGGTCCACCTGCCCCAAAGGCGGACGCAGGAC

AGTAGAAGGGAACAGAGAACACATAAACACAGAGAGGGCCACAGCGGCTC

CCACAGTCACCGCCACCTTCCTGGCGGGGATGGGTGGGGCGTCTGAGTTT

GGTTCCCAGCAAATCCCTCTGAGCCGCCCTTGCGGGCTCGCCTCAGGAGC

AGGGGAGCAAGAGGTGGGAGGAGGAGGTCTAAGTCCCAGGCCCAATTAAG

AGATCAGGTAGTGTAGGGTTTGGGAGCTTTTAAGGTGAAGAGGCCCGGGC

TGATCCCACAGGCCAGTATAAAGCGCCGTGACCCTCAGGTGATGCGCCAG

GGCCGGCTGCCTGCGGGACAGGGCTTTCCATAGCCATGAGGATCCGAAT

TCGGATCCC
```

Exemplary M-opsin genes include mouse M-opsin and human M-opsin. Exemplary nucleotide sequences of M-opsin genes are provided below.

```
Exemplary mouse m-opsin nucleotide sequence:
                                        (SEQ ID NO: 3)
CAGAGACAGT TTTCTACAGC CATGGCCCAA AGGCTTACAG

GTGAACAGAC ACTGGACCAC TATGAGGATA GCACCCATGC

AAGCATCTTC ACCTATACCA ACAGCAACAG CACCAAAGGT

CCCTTTGAAG GCCCCAATTA TCACATTGCT CCCAGGTGGG

TGTACCACCT CACCAGCACC TGGATGATTC TTGTGGTCGT

TGCATCTGTC TTCACTAATG GACTTGTGCT GGCAGCCACC

ATGAGATTCA AGAAGCTGCG CCATCCACTG AACTGGATTC

TGGTGAACTT GGCAGTTGCT GACCTAGCAG AGACCATTAT

TGCCAGCACT ATCAGTGTTG TGAACCAAAT CTATGGCTAC

TTCGTTCTGG GACACCCTCT GTGTGTCATT GAAGGCTACA

TTGTCTCATT GTGTGGAATC ACAGGCCTCT GGTCCCTGGC

CATCATTTCC TGGGAGAGAT GGCTGGTGGT CTGCAAGCCC

TTTGGCAATG TGAGATTTGA TGCTAAGCTG GCCACTGTGG

GAATCGTCTT CTCCTGGGTC TGGGCTGCTA TATGGACGGC

CCCACCAATC TTTGGTTGGA GCAGGTACTG GCCTTATGGC

CTGAAGACAT CCTGTGGCCC AGACGTGTTC AGCGGTACCT
```

```
CGTACCCCGG GGTTCAGTCT TATATGATGG TCCTCATGGT
CACGTGCTGC ATCTTCCCAC TCAGCATCAT CGTGCTCTGC
TACCTCCAAG TGTGGCTGGC CATCCGAGCA GTGGCAAAGC
AACAGAAAGA ATCTGAGTCC ACTCAGAAGG CCGAGAAGGA
GGTGACACGC ATGGTGGTGG TGATGGTCTT CGCATACTGC
CTCTGCTGGG GACCCTATAC TTTCTTTGCA TGCTTTGCTA
CTGCCCACCC TGGCTATGCC TTCCACCCTC TTGTGGCCTC
CCTACCATCC TACTTTGCCA AAAGTGCCAC TATCTACAAC
CCCATTATCT ATGTCTTTAT GAACCGGCAG TTTCGAAACT
GCATCTTACA TCTCTTTGGA AAGAAGGTTG ATGATAGCTC
TGAACTTTCC AGCACCTCCA AGACAGAAGT CTCATCTGTC
TCTTCAGTGT CACCTGCATA A
Exemplary human M-opsin nucleotide sequence:
                                     (SEQ ID NO: 4)
ATGGCCCA GCAGTGGAGC CTCCAAAGGC TCGCAGGCCG
CCATCCGCAG GACAGCTATG AGGACAGCAC CCAGTCCAGC
ATCTTCACCT ACACCAACAG CAACTCCACC AGAGGCCCCT
TCGAAGGCCC GAATTACCAC ATCGCTCCCA GATGGGTGTA
CCACCTCACC AGTGTCTGGA TGATCTTTGT GGTCATTGCA
TCCGTCTTCA CAAATGGGCT TGTGCTGGCG GCCACCATGA
AGTTCAAGAA GCTGCGCCAC CCGCTGAACT GGATCCTGGT
GAACCTGGCG GTCGCTGACC TGGCAGAGAC CGTCATCGCC
AGCACTATCA GCGTTGTGAA CCAGGTCTAT GGCTACTTCG
TGCTGGGCCA CCCCTATGTG TCCTGGAGG GCTACACCGT
CTCCCTGTGT GGGATCACAG GTCTCTGGTC TCTGGCCATC
ATTTCCTGGG AGAGATGGAT GGTGGTCTGC AAGCCCTTTG
GCAATGTGAG ATTTGATGCC AAGCTGGCCA TCGTGGGCAT
TGTCTTCTCC TGGATCTGGT CTGCTGTGTG GACAGCCCCG
CCCATCTTTG GTTGGAGCAG GTACTGGCCC CACGGCCTGA
AGACTTCATG CGGCCCAGAC GTGTTCAGCG GCAGCTCGTA
CCCCGGGGTG CAGTCTTACA TGATTGTCCT CATGGTCACC
TGCTGCATCA CCCCACTCAG CATCATCGTG CTCTGCTACC
TCCAAGTGTG GCTGGCCATC CGAGCGGTGG CAAAGCAGCA
GAAAGAGTCT GAATCCACCC AGAAGGCAGA AAGGAAGTG
ACGCGCATGG TGGTGGTGAT GGTCCTGGCA TTCTGCTTCT
GCTGGGGACC ATACGCCTTC TTCGCATGCT TTGCTGCTGC
CAACCCTGGC TACCCCTTCC ACCCTTTGAT GGCTGCCCTG
CCGGCCTTCT TTGCCAAAAG TGCCACTATC TACAACCCCG
TTATCTATGT CTTTATGAAC CGGCAGTTTC GAAACTGCAT
CTTGCAGCTT TTCGGGAAGA AGGTTGACGA TGGCTCTGAA
CTCTCCAGCG CCTCCAAAAC GGAGGTCTCA TCTGTGTCCT
CGGTATCGCC TGCATGA
```

In some embodiments, the M-opsin gene comprises a nucleotide sequence that encodes an M-opsin protein, such as mouse M-opsin or human M-opsin protein. Exemplary M-opsin protein sequences are provided below.

```
Mouse m-opsin amino acid sequence:
                                     (SEQ ID NO: 5)
MAQRLTGEQTLDHYEDSTHASIFTYTNSNSTKGPFEGPNYHIAPRWVYHL
TSTWMILVVVASVFTNGLVLAATMRFKKLRHPLNWILVNLAVADLAETII
ASTISVVNQIYGYFVLGHPLCVIEGYIVSLCGITGLWSLAIISWERWLVV
CKPFGNVRFDAKLATVGIVFSWVWAAIWTAPPIFGWSRYWPYGLKTSCGP
DVFSGTSYPGVQSYMMVLMVTCCIFPLSIIVLCYLQVWLAIRAVAKQQKE
SESTQKAEKEVTRMVVVMVFAYCLCWGPYTFFACFATAHPGYAFHPLVAS
LPSYFAKSATIYNPIIYVFMNRQFRNCILHLFGKKVDDSSELSSTSKTEV
SSVSSVSPA Human m-opsin amino acid sequence:
                                     (SEQ ID NO: 6)
MAQQWSLQRLAGRHPQDSYEDSTQSSIFTYTNSNSTRGPFEGPNYHIAPR
WVYHLTSVWMIFVVIASVFTNGLVLAATMKFKKLRHPLNWILVNLAVADL
AETVIASTISVVNQVYGYFVLGHPMCVLEGYTVSLCGITGLWSLAIISWE
RWMVVCKPFGNVRFDAKLAIVGIVFSWIWSAVWTAPPIFGWSRYWPHGLK
TSCGPDVFSGSSYPGVQSYMIVLMVTCCITPLSIIVLCYLQVWLAIRAVA
KQQKESESTQKAEKEVTRMVVVMVLAFCFCWGPYAFFACFAAANPGYPFH
PLMAALPAFFAKSATIYNPVIYVFMNRQFRNCILQLFGKKVDDGSELSSA
SKTEVSSVSSVSPA
```

In some embodiments, the expression construct further contains nucleic acid segments that encode one or more (e.g., one, two, or three) polyadenylation signals. In some embodiments, the expression construct further contains nucleic acid segments that encode an SV40 polyadenylation signal and/or a bovine growth hormone (BGH) polyadenylation signal. In some embodiments, the nucleic acid segments are positioned 3' to the opsin gene (e.g., the M-opsin gene) in the expression construct. Exemplary SV40 and BGH polyadenylation sequences are provided below.

```
Exemplary SV40 polyA sequence
                                     (SEQ ID NO: 7)
CGGGGATCCAGACATGATAAGATACATTGATGAGTTTGGACAAACCACAA
CTAGAATGCAGTGAAAAAAATGCTTTATTTGTGAAATTTGTGATGCTATT
GCTTTATTTGTAACCATTATAAGCTGCAATAAACAAGTTAACAACAACAA
TTGCATTCATTTTATGTTTCAGGTTCAGGGGGAGGTGTGGGAGGTTTTT Exemplary BGH polyA sequence
                                     (SEQ ID NO: 8)
GCTGATCAGCCTCGACTGTGCCTTCTAGTTGCCAGCCATCTGTTGTTTGC
CCCTCCCCCGTGCCTTCCTTGACCCTGGAAGGTGCCACTCCCACTGTCCT
TTCCTAATAAAATGAGGAAATTGCATCGCATTGTCTGAGTAGGTGTCATT
```

-continued
CTATTCTGGGGGGTGGGGTGGGGCAGGACAGCAAGGGGGAGGATTGGGAA

GACAATAGCAGGCATGCTGGGGA

In some embodiments, the nucleic acid is a plasmid. In some embodiments, the nucleic acid comprises or consists of the sequence of SEQ ID NO: 2.

Exemplary plasmid sequence
(SEQ ID NO: 2)
TTGGCCACTCCCTCTCTGCGCGCTCGCTCGCTCACTGAGGCCGGGCGACC

AAAGGTCGCCCGACGCCCGGGCTTTGCCCGGGCGGCCTCAGTGAGCGAGC

GAGCGCGCAGAGAGGGAGTGGCCAACTCCATCACTAGGGGTTCCTAGATC

TGAATTCGGTACCCCCGGGGGATCCTCTAGAGTCGACAGGCCTACAGCAG

CCAGGGTGAGATTATGAGGCTGAGCTGAGAATATCAAGACTGTACCGAGT

AGGGGGCCTTGGCAAGTGTGGAGAGCCCGGCAGCTGGGGCAGAGGGCGGA

GTACGGTGTGCGTTTACGGACCTCTTCAAACGAGGTAGGAAGGTCAGAAG

TCAAAAAGGGAACAAATGATGTTTAACCACACAAAAATGAAAATCCAATG

GTTGGATATCCATTCCAAATACACAAAGGCAACGGATAAGTGATCCGGGC

CAGGCACAGAAGGCCATGCACCCGTAGGATTGCACTCAGAGCTCCCAAAT

GCATAGGAATAGAAGGGTGGGTGCAGGAGGCTGAGGGGTGGGAAAGGGC

ATGGGTGTTTCATGAGGACAGAGCTTCCGTTTCATGCAATGAAAAGAGTT

TGGAGACGGATGGTGGTGACTGGACTATACACTTACACACGGTAGCGATG

GTACACTTTGTATTATGTATATTTTACCACGATCTTTTTAAAGTGTCAAA

GGCAAATGGCCAAATGGTTCCTTGTCCTATAGCTGTAGCAGCCATCGGCT

GTTAGTGACAAAGCCCCTGAGTCAAGATGACAGCAGCCCCCATAACTCCT

AATCGGCTCTCCCGCGTGGAGTCATTTAGGAGTAGTCGCATTAGAGACAA

GTCCAACATCTAATCTTCCACCCTGCCAGGGCCCCAGCTGGCAGCGAGGG

TGGGAGACTCCGGGCAGAGCAGAGGGCGCTGACATTGGGGCCCGGCCTGG

CTTGGGTCCCTCTGGCCTTTCCCCAGGGGCCCTCTTTCCTTGGGGCTTTC

TTGGGCCGCCACTGCTCCCGCTCCTCTCCCCCCATCCCACCCCCTCACCC

CCTCGTTCTTCATATCCTTCTCTAGTGCTCCCTCCACTTTCATCCACCCT

TCTGCAAGAGTGTGGGACCACAAATGAGTTTTCACCTGGCCTGGGGACAC

ACGTGCCCCACAGGTGCTGAGTGACTTTCTAGGACAGTAATCTGCTTTA

GGCTAAAATGGGACTTGATCTTCTGTTAGCCCTAATCATCAATTAGCAGA

GCCGGTGAAGGTGCAGAACCTACCGCCTTTCCAGGCCTCCTCCCACCTCT

GCCACCTCCACTCTCCTTCCTGGGATGTGGGGGCTGGCACACGTGTGGCC

CAGGGCATTGGTGGGATTGCACTGAGCTGGGTCATTAGCGTAATCCTGGA

CAAGGGCAGACAGGGCGAGCGGAGGGCCAGCTCCGGGGCTCAGGCAAGGC

TGGGGGCTTCCCCCAGACACCCCACTCCTCCTCTGCTGGACCCCCACTTC

ATAGGGCACTTCGTGTTCTCAAAGGGCTTCCAAATAGCATGGTGGCCTTG

GATGCCCAGGGAAGCCTCAGAGTTGCTTATCTCCCTCTAGACAGAAGGGG

AATCTCGGTCAAGAGGGAGAGGTCGCCCTGTTCAAGGCCACCCAGCCAGC

TCATGGCGGTAATGGGACAAGGCTGGCCAGCCATCCCACCCTCAGAAGGG

ACCCGGTGGGGCAGGTGATCTCAGAGGAGGCTCACTTCTGGGTCTCACAT

TCTTGGATCCGGTTCCAGGCCTCGGCCCTAAATAGTCTCCCTGGGCTTTC

AAGAGAACCACATGAGAAAGGAGGATTCGGGCTCTGAGCAGTTTCACCAC

CCACCCCCCAGTCTGCAAATCCTGACCCGAGGGTCCACCTGCCCCAAAGG

CGGACGCAGGACAGTAGAAGGGAACAGAGAACACATAAACACAGAGAGGG

CCACAGCGGCTCCCACAGTCACCGCCACCTTCCTGGCGGGGATGGGTGGG

GCGTCTGAGTTTGGTTCCCAGCAAATCCCTCTGAGCCGCCCTTGCGGGCT

CGCCTCAGGAGCAGGGGAGCAAGAGGTGGGAGGAGGAGGTCTAAGTCCCA

GGCCCAATTAAGAGATCAGGTAGTGTAGGGTTTGGGAGCTTTTAAGGTGA

AGAGGCCCGGGCTGATCCCACAGGCCAGTATAAAGCGCCGTGACCCTCAG

GTGATGCGCCAGGGCCGGCTGCCTGCGGGGACAGGGCTTTCCATAGCCAT

GAGGATCCGAATTCGGATCCCCATGTCTAGAGGATCCGGTACTCGAGGAA

CTGAAAAACCAGAAAGTTAACTGGTAAGTTTAGTCTTTTTGTCTTTTATT

TCAGGTCCCGGATCCGGTGGTGGTGCAAATCAAAGAACTGCTCCTCAGTG

GATGTTGCCTTTACTTCTAGGCCTGTACGGAAGTGTTACTTCTGCTCTAA

AAGCTGCGGAATTGTACCCGCGGCCGCCACCATGGCCCAAAGGCTTACAG

GTGAACAGACACTGGACCACTATGAGGATAGCACCCATGCAAGCATCTTC

ACCTATACCAACAGCAACAGCACCAAAGGTCCCTTTGAAGGCCCCAATTA

TCACATTGCTCCCAGGTGGGTGTACCACCTCACCAGCACCTGGATGATTC

TTGTGGTCGTTGCATCTGTCTTCACTAATGGACTTGTGCTGGCAGCCACC

ATGAGATTCAAGAAGCTGCGCCATCCACTGAACTGGATTCTGGTGAACTT

GGCAGTTGCTGACCTAGCAGAGACCATTATTGCCAGCACTATCAGTGTTG

TGAACCAAATCTATGGCTACTTCGTTCTGGGACACCCTCTGTGTGTCATT

GAAGGCTACATTGTCTCATTGTGTGGAATCACAGGCCTCTGGTCCCTGGC

CATCATTTCCTGGGAGAGATGGCTGGTGGTCTGCAAGCCCTTTGGCAATG

TGAGATTTGATGCTAAGCTGGCCACTGTGGGAATCGTCTTCTCCTGGGTC

TGGGCTGCTATATGGACGGCCCCACCAATCTTTGGTTGGAGCAGGTACTG

GCCTTATGGCCTGAAGACATCCTGTGGCCCAGACGTGTTCAGCGGTACCT

CGTACCCCGGGGTTCAGTCTTATATGATGGTCCTCATGGTCACGTGCTGC

ATCTTCCCACTCAGCATCATCGTGCTCTGCTACCTCCAAGTGTGGCTGGC

CATCCGAGCAGTGGCAAAGCAACAGAAAGAATCTGAGTCCACTCAGAAGG

CCGAGAAGGAGGTGACACGCATGGTGGTGGTGATGGTCTTCGCATACTGC

CTCTGCTGGGGACCCTATACTTTCTTTGCATGCTTTGCTACTGCCCACCC

TGGCTATGCCTTCCACCCTCTTGTGGCCTCCCTACCATCCTACTTTGCCA

AAAGTGCCACTATCTACAACCCCATTATCTATGTCTTTATGAACCGGCAG

TTTCGAAACTGCATCTTACATCTCTTTGGAAAGAAGGTTGATGATAGCTC

TGAACTTTCCAGCACCTCCAAGACAGAAGTCTCATCTGTCTCTTCAGTGT

CACCTGCATAAGCGGCCGCGGGGATCCAGACATGATAAGATACATTGATG

AGTTTGGACAAACCACAACTAGAATGCAGTGAAAAAAATGCTTTATTTGT

GAAATTTGTGATGCTATTGCTTTATTTGTAACCATTATAAGCTGCAATAA

ACAAGTTAACAACAACAATTGCATTCATTTTATGTTTCAGGTTCAGGGGG

```
AGGTGTGGGAGGTTTTTTAGTCGACTAGAGCTCGCTGATCAGCCTCGACT
GTGCCTTCTAGTTGCCAGCCATCTGTTGTTTGCCCCTCCCCCGTGCCTTC
CTTGACCCTGGAAGGTGCCACTCCCACTGTCCTTTCCTAATAAAATGAGG
AAATTGCATCGCATTGTCTGAGTAGGTGTCATTCTATTCTGGGGGGTGGG
GTGGGGCAGGACAGCAAGGGGGAGGATTGGGAAGACAATAGCAGGCATGC
TGGGGAGAGATCTAGGAACCCCTAGTGATGGAGTTGGCCACTCCCTCTCT
GCGCGCTCGCTCGCTCACTGAGGCCGCCCGGGCAAAGCCCGGGCGTCGGG
CGACCTTTGGTCGCCCGGCCTCAGTGAGCGAGCGAGCGCGCAGAGAGGGA
GTGGCCAACCCCCCCCCCCCCCCCCCCCTGCAGCCCTGCATTAATGAATCGG
CCAACGCGCGGGGAGAGGCGGTTTGCGTATTGGGCGCTCTTCCGCTTCCT
CGCTCACTGACTCGCTGCGCTCGGTCGTTCGGCTGCGGCGAGCGGTATCA
GCTCACTCAAAGGCGGTAATACGGTTATCCACAGAATCAGGGGATAACGC
AGGAAAGAACATGTGAGCAAAAGGCCAGCAAAAGGCCAGGAACCGTAAAA
AGGCCGCGTTGCTGGCGTTTTTCCATAGGCTCCGCCCCCCTGACGAGCAT
CACAAAAATCGACGCTCAAGTCAGAGGTGGCGAAACCCGACAGGACTATA
AAGATACCAGGCGTTTCCCCCTGGAAGCTCCCTCGTGCGCTCTCCTGTTC
CGACCCTGCCGCTTACCGGATACCTGTCCGCCTTTCTCCCTTCGGGAAGC
GTGGCGCTTTCTCAATGCTCACGCTGTAGGTATCTCAGTTCGGTGTAGGT
CGTTCGCTCCAAGCTGGGCTGTGTGCACGAACCCCCGTTCAGCCCGACC
GCTGCGCCTTATCCGGTAACTATCGTCTTGAGTCCAACCCGGTAAGACAC
GACTTATCGCCACTGGCAGCAGCCACTGGTAACAGGATTAGCAGAGCGAG
GTATGTAGGCGGTGCTACAGAGTTCTTGAAGTGGTGGCCTAACTACGGCT
ACACTAGAAGGACAGTATTTGGTATCTGCGCTCTGCTGAAGCCAGTTACC
TTCGGAAAAAGAGTTGGTAGCTCTTGATCCGGCAAACAAACCACCGCTGG
TAGCGGTGGTTTTTTTGTTTGCAAGCAGCAGATTACGCGCAGAAAAAAAG
GATCTCAAGAAGATCCTTTGATCTTTTCTACGGGGTCTGACGCTCAGTGG
AACGAAAACTCACGTTAAGGGATTTTGGTCATGAGATTATCAAAAAGGAT
CTTCACCTAGATCCTTTTAAATTAAAAATGAAGTTTTAAATCAATCTAAA
GTATATATGAGTAAACTTGGTCTGACAGTTACCAATGCTTAATCAGTGAG
GCACCTATCTCAGCGATCTGTCTATTTCGTTCATCCATAGTTGCCTGACT
CCCCGTCGTGTAGATAACTACGATACGGGAGGGCTTACCATCTGGCCCCA
GTGCTGCAATGATACCGCGAGACCCACGCTCACCGGCTCCAGATTTATCA
GCAATAAACCAGCCAGCCGGAAGGGCCGAGCGCAGAAGTGGTCCTGCAAC
TTTATCCGCCTCCATCCAGTCTATTAATTGTTGCCGGGAAGCTAGAGTAA
GTAGTTCGCCAGTTAATAGTTTGCGCAACGTTGTTGCCATTGCTACAGGC
ATCGTGGTGTCACGCTCGTCGTTTGGTATGGCTTCATTCAGCTCCGGTTC
CCAACGATCAAGGCGAGTTACATGATCCCCCATGTTGTGCAAAAAAGCGG
TTAGCTCCTTCGGTCCTCCGATCGTTGTCAGAAGTAAGTTGGCCGCAGTG
TTATCACTCATGGTTATGGCAGCACTGCATAATTCTCTTACTGTCATGCC
ATCCGTAAGATGCTTTTCTGTGACTGGTGAGTACTCAACCAAGTCATTCT
GAGAATAGTGTATGCGGCGACCGAGTTGCTCTTGCCCGGCGTCAATACGG
GATAATACCGCGCCACATAGCAGAACTTTAAAAGTGCTCATCATTGGAAA
ACGTTCTTCGGGGCGAAAACTCTCAAGGATCTTACCGCTGTTGAGATCCA
GTTCGATGTAACCCACTCGTGCACCCAACTGATCTTCAGCATCTTTTACT
TTCACCAGCGTTTCTGGGTGAGCAAAAACAGGAAGGCAAAATGCCGCAAA
AAAGGGAATAAGGGCGACACGGAAATGTTGAATACTCATACTCTTCCTTT
TTCAATATTATTGAAGCATTTATCAGGGTTATTGTCTCATGAGCGGATAC
ATATTTGAATGTATTTAGAAAAATAAACAAATAGGGGTTCCGCGCACATT
TCCCCGAAAAGTGCCACCTGACGTCTAAGAAACCATTATTATCATGACAT
TAACCTATAAAAATAGGCGTATCACGAGGCCCTTTCGTCTCGCGCGTTTC
GGTGATGACGGTGAAAACCTCTGACACATGCAGCTCCCGGAGACGGTCAC
AGCTTGTCTGTAAGCGGATGCCGGGAGCAGACAAGCCCGTCAGGGCGCGT
CAGCGGGTGTTGGCGGGTGTCGGGGCTGGCTTAACTATGCGGCATCAGAG
CAGATTGTACTGAGAGTGCACCATATGCGGTGTGAAATACCGCACAGATG
CGTAAGGAGAAAATACCGCATCAGGAAATTGTAAACGTTAATATTTTGTT
AAAATTCGCGTTAAATTTTTGTTAAATCAGCTCATTTTTTAACCAATAGG
CCGAAATCGGCAAAATCCCTTATAAATCAAAAGAATAGACCGAGATAGGG
TTGAGTGTTGTTCCAGTTTGGAACAAGAGTCCACTATTAAAGAACGTGGA
CTCCAACGTCAAAGGGCGAAAAACCGTCTATCAGGGCGATGGCCCACTAC
GTGAACCATCACCCTAATCAAGTTTTTTGGGGTCGAGGTGCCGTAAAGCA
CTAAATCGGAACCCTAAAGGGAGCCCCCGATTTAGAGCTTGACGGGGAAA
GCCGGCGAACGTGGCGAGAAAGGAAGGGAAGAAAGCGAAAGGAGCGGGCG
CTAGGGCGCTGGCAAGTGTAGCGGTCACGCTGCGCGTAACCACCACACCC
GCCGCGCTTAATGCGCCGCTACAGGGCGCGTCGCGCCATTCGCCATTCAG
GCTACGCAACTGTTGGGAAGGGCGATCGGTGCGGGCCTCTTCGCTATTAC
GCCAGGCTGCAGGGGGGGGGGGGGGGGG
```

In some embodiments, the nucleic acid is a recombinant adeno-associated virus (rAAV) vector. Exemplary rAAV nucleic acid vectors useful according to the disclosure include single-stranded (ss) or self-complementary (sc) AAV nucleic acid vectors.

In some embodiments, a recombinant rAAV particle comprises a nucleic acid vector, such as a single-stranded (ss) or self-complementary (sc) AAV nucleic acid vector. In some embodiments, the nucleic acid vector contains an expression construct comprising an opsin gene (e.g., an M-opsin gene) operably linked to a cone-specific promoter and one or more regions comprising inverted terminal repeat (ITR) sequences (e.g., wild-type ITR sequences or engineered ITR sequences) flanking the expression construct. In some embodiments, the nucleic acid is encapsidated by a viral capsid. In some embodiments, a nucleic acid vector is a linear nucleic acid vector (e.g., a single-stranded or double-stranded linear nucleic acid, for example containing an expression cassette flanked by ITRs).

Accordingly, in some embodiments, an rAAV particle comprises a viral capsid and a nucleic acid vector as described herein, which is encapsidated by the viral capsid. In some embodiments, the viral capsid comprises 60 capsid protein subunits comprising VP1, VP2 and VP3. In some embodiments, the VP1, VP2, and VP3 subunits are present in the capsid at a ratio of approximately 1:1:10, respectively.

The ITR sequences of a nucleic acid or nucleic acid vector described herein can be derived from any AAV serotype (e.g., 1, 2, 3, 4, 5, 6, 7, 8, 9, or 10) or can be derived from more than one serotype. In some embodiments of the nucleic acid or nucleic acid vector provided herein, the ITR sequences are derived from AAV2. ITR sequences and plasmids containing ITR sequences are known in the art and commercially available (see, e.g., products and services available from Vector Biolabs, Philadelphia, Pa.; Cellbiolabs, San Diego, Calif.; Agilent Technologies, Santa Clara, Calif.; and Addgene, Cambridge, Mass.; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. Proc Natl Acad Sci USA. 1996 Nov. 26; 93(24):14082-7; and Curtis A. Machida. Methods in Molecular Medicine™. Viral Vectors for Gene Therapy Methods and Protocols. 10.1385/1-59259-304-6: 201 © Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference).

In some embodiments, the nucleic acid or nucleic acid vector comprises a pTR-UF-11 plasmid backbone, which is a plasmid that contains AAV2 ITRs, or a nucleic acid region of the pTR-UF-11 plasmid that comprises the ITRs. This plasmid is commercially available from the American Type Culture Collection (ATCC MBA-331).

In some embodiments, the expression construct is no more than 6 kilobases, no more than 5 kilobases, no more than 4 kilobases, or no more than 3 kilobases in size. In some embodiments, the expression construct is between 4 and 6 kilobases in size, e.g., 4-6 kilobases, 4-5 kilobases, or 4.2-4.7 kilobases in size.

In some embodiments, the expression construct comprises one or more regions comprising a sequence that facilitates expression of the opsin gene, e.g., expression control sequences operably linked to the opsin gene. Non-limiting examples of expression control sequences include promoters, insulators, silencers, response elements, introns, enhancers, initiation sites, termination signals, and poly(A) tails. Any combination of such control sequences is contemplated herein (e.g., a promoter and an enhancer). In some embodiments, the promoter is a cone-specific promoter, such as a PR2.1 promoter as described herein. In some embodiments, the expression construct contains a splice donor/acceptor site, such as between the promoter and opsin gene.

In some embodiments, a nucleic acid described herein, such as a plasmid, may also contain marker or reporter genes, e.g., LacZ or a fluorescent protein, and an origin of replication (e.g. an fl(+) origin and/or a ColE1 origin).

The rAAV particle may be of any AAV serotype (e.g., 1, 2, 3, 4, 5, 6, 7, 8, 9, or 10), including any derivative or pseudotype. Non-limiting examples of derivatives and pseudotypes include AAV2-AAV3 hybrid, AAVrh.10, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6 (Y445F/Y731F), AAV2.5T, AAV-HAE1/2, AAV clone 32/83, AAVShH10, AAV2 (Y→F), AAV8 (Y733F), AAV2.15, AAV2.4, AAVM41, and AAVr3.45. Such AAV serotypes and derivatives/pseudotypes, and methods of producing such derivatives/pseudotypes are known in the art (see, e.g., Mol Ther. 2012 April; 20(4):699-708. doi: 10.1038/mt.2011.287. Epub 2012 Jan. 24. The AAV vector toolkit: poised at the clinical crossroads. Asokan A1, Schaffer D V, Samulski R J.). In some embodiments, the rAAV particle is a pseudotyped rAAV particle, which comprises (a) a nucleic acid vector comprising ITRs from one serotype (e.g., AAV2) and (b) a capsid comprised of capsid proteins derived from another serotype (e.g., AAV1, AAV3, AAV4, AAV5, AAV6, AAV7, AAV8, AAV9, or AAV10). Methods for producing and using pseudotyped rAAV vectors are known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001).

In some embodiments, the rAAV particle is AAV5. In some embodiments, the rAAV particle comprises AAV5 capsid proteins. In some embodiments, the rAAV particle comprises wild-type AAV5 capsid proteins. In some embodiments, the rAAV particle comprises variant AAV5 capsid proteins, e.g., AAV5 capsid proteins that contain one or more modifications compared to the wild-type capsid protein sequence. Such one or more modifications can include but are not limited to, one or more amino acid modifications (e.g., one or more amino acid substitutions, one or more amino acid insertions, one or more amino acid deletions, or some combination thereof) with respect to the wild-type AAV5 capsid protein sequence. In some embodiments, the AAV5 capsid protein comprises 1, 2, 3, 4, 5, 6, 7, 8, 9, 10, 15, 20 or more amino acid modifications (e.g., 1, 2, 3, 4, 5, 6, 7, 8, 9, 10, 15, 20 or more amino acid substitutions; 1, 2, 3, 4, 5, 6, 7, 8, 9, 10, 15, 20 or more amino acid insertions; 1, 2, 3, 4, 5, 6, 7, 8, 9, 10, 15, 20 or more amino acid deletions; or some combination thereof) with respect to the wild-type AAV5 capsid protein sequence. An exemplary, non-limiting wild-type AAV5 capsid protein sequence is provided below.

```
Exemplary AAV5 capsid protein
                                                      (SEQ ID NO: 9)
  1 MSFVDHPPDW LEEVGEGLRE FLGLEAGPPK PKPNQQHQDQ ARGLVLPGYN

51 YLGPGNGLDR GEPVNRADEV AREHDISYNE QLEAGDNPYL KYNHADAEFQ

101 EKLADDTSFG GNLGKAVFQA KKRVLEPFGL VEEGAKTAPT GKRIDDHFPK

151 RKKARTEEDS KPSTSSDAEA GPSGSQQLQI PAQPASSLGA DTMSAGGGGP

201 LGDNNQGADG VGNASGDWHC DSTWMGDRVV TKSTRTWVLP SYNNHQYREI

251 KSGSVDGSNA NAYFGYSTPW GYFDFNRFHS HWSPRDWQRL INNYWGFRPR

301 SLRVKIFNIQ VKEVTVQDST TTIANNLTST VQVFTDDDYQ LPYVVGNGTE

351 GCLPAFPPQV FTLPQYGYAT LNRDNTENPT ERSSFFCLEY FPSKMLRTGN
```

```
-continued
401 NFEFTYNFEE VPFHSSFAPS QNLFKLANPL VDQYLYRFVS TNNTGGVQFN

451 KNLAGRYANT YKNWFPGPMG RTQGWNLGSG VNRASVSAFA TTNRMELEGA

501 SYQVPPQPNG MTNNLQGSNT YALENTMIFN SQPANPGTTA TYLEGNMLIT

551 SESETQPVNR VAYNVGGQMA TNNQSSTTAP ATGTYNLQEI VPGSVWMERD

601 VYLQGPIWAK IPETGAHFHP SPAMGGFGLK HPPPMMLIKN TPVPGNITSF

651 SDVPVSSFIT QYSTGQVTVE MEWELKKENS KRWNPEIQYT NNYNDPQFVD

701 FAPDSTGEYR TTRPIGTRYL TRPL
```

Methods of producing rAAV particles and nucleic acid vectors are also known in the art and commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). For example, the nucleic acid vector may be combined with one or more helper plasmids, e.g., that contain a rep gene (e.g., encoding Rep78, Rep68, Rep52 and Rep40) and a cap gene (encoding VP1, VP2, and VP3), and transfected into a producer cell line such that the rAAV particle can be packaged and subsequently purified.

In some embodiments, the one or more helper plasmids includes a first helper plasmid comprising a rep gene and a cap gene and a second helper plasmid comprising other genes that assist in AAV production, such as a E1a gene, a E1b gene, a E4 gene, a E2a gene, and a VA gene. In some embodiments, the rep gene is a rep gene derived from AAV2 and the cap gene is derived from AAV5. Helper plasmids, and methods of making such plasmids, are known in the art and commercially available (see, e.g., pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, Pa.; Cellbiolabs, San Diego, Calif.; Agilent Technologies, Santa Clara, Calif.; and Addgene, Cambridge, Mass.; pxx6; Grimm et al. (1998), Novel Tools for Production and Purification of Recombinant Adenoassociated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188).

An exemplary, non-limiting, rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. HEK293 cells (available from ATCC®) are transfected via CaPO$_4$-mediated transfection, lipids or polymeric molecules such as Polyethylenimine (PEI) with the helper plasmid(s) and a plasmid containing a nucleic acid vector described herein. Alternatively, in another example, Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known the art or described herein, e.g., by iodixanol step gradient, CsCl gradient, chromatography, or polyethylene glycol (PEG) precipitation.

The disclosure also contemplates host cells that comprise at least one of the disclosed rAAV particles or nucleic acid vectors. Such host cells include mammalian host cells, with human host cells being preferred, and may be either isolated, in cell or tissue culture. In the case of genetically modified animal models (e.g., a mouse), the transformed host cells may be comprised within the body of a non-human animal itself.

Compositions

Aspects of the disclosure relate to compositions comprising rAAV particles or nucleic acids described herein. In some embodiments, rAAV particles described herein are added to a composition, e.g., a pharmaceutical composition.

In some embodiments, the composition comprises a pharmaceutically acceptable carrier. The term "carrier" refers to a diluent, adjuvant, excipient, or vehicle with which the rAAV particle is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers. Non-limiting examples of pharmaceutically acceptable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, polyacrylic acids, lubricating agents (such as talc, magnesium stearate, and mineral oil), wetting agents, emulsifying agents, suspending agents, preserving agents (such as methyl-, ethyl-, and propyl-hydroxy-benzoates), and pH adjusting agents (such as inorganic and organic acids and bases). Other exemplary carriers that might be used include saline (e.g., sterilized, pyrogen-free saline), saline buffers (e.g., citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade carriers and excipients are particularly useful for delivery of rAAV particles to human subjects. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Methods for making such compositions are well known and can be found in, for example, Remington: The Science and Practice of Pharmacy, $22^{nd}$ edition, Pharmaceutical Press, 2012.

Typically, such compositions may contain at least about 0.1% of the therapeutic agent (e.g., rAAV particle) or more, although the percentage of the active ingredient(s) may, of course, be varied and may conveniently be between about 1 or 2% and about 70% or 80% or more of the weight or volume of the total formulation. Naturally, the amount of therapeutic agent(s) (e.g., rAAV particle) in each therapeutically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, a composition described herein may be administered to a subject in need thereof, such as a subject having BCM. In some embodiments, a method described herein may comprise administering a composition comprising rAAV particles as described herein to a subject in need thereof. In some embodiments, the subject is a human subject. In some embodiments, the subject has or is suspected of having a disease that may be treated with gene therapy, such as BCM.

Methods

Aspects of the disclosure relate to treatment of ocular disorders such as cone monochromacies (e.g., blue cone monochromacy) and cone dichromacies (e.g., protanopia or deuteranopia). In some embodiments, the method comprises administering a therapeutically effective amount of an rAAV particle or a composition as described herein to a subject having a cone monochromacy or dichromacy.

To "treat" a disease as the term is used herein, means to reduce the frequency or severity of at least one sign or symptom of a disease or disorder experienced by a subject. The compositions described above are typically administered to a subject in an effective amount, that is, an amount capable of producing a desirable result. The desirable result will depend upon the active agent being administered. For example, an effective amount of rAAV particles may be an amount of the particles that are capable of transferring an expression construct to a host organ, tissue, or cell. A therapeutically acceptable amount may be an amount that is capable of treating a disease, e.g., BCM. As is well known in the medical and veterinary arts, dosage for any one subject depends on many factors, including the subject's size, body surface area, age, the particular composition to be administered, the active ingredient(s) in the composition, time and route of administration, general health, and other drugs being administered concurrently.

The rAAV particle or nucleic acid vector may be delivered in the form of a composition, such as a composition comprising the active ingredient, such as an rAAV particle described herein, and a pharmaceutically acceptable carrier as described herein. The rAAV particles or nucleic acid vectors may be prepared in a variety of compositions, and may also be formulated in appropriate pharmaceutical vehicles for administration to human or animal subjects.

In some embodiments, the number of rAAV particles administered to a subject may be on the order ranging from $10^6$ to $10^{14}$ particles/mL or $10^3$ to $10^{15}$ particles/mL, or any values therebetween for either range, such as for example, about $10^6$, $10^7$, $10^8$, $10^9$, $10^{10}$, $10^{11}$, $10^{12}$, $10^{13}$, or $10^{14}$ particles/mL. In one embodiment, rAAV particles of higher than $10^{13}$ particles/mL are administered. In some embodiments, the number of rAAV particles administered to a subject may be on the order ranging from $10^6$ to $10^{14}$ vector genomes (vgs)/mL or $10^3$ to $10^{15}$ vgs/mL, or any values therebetween for either range, such as for example, about $10^6$, $10^7$, $10^8$, $10^9$, $10^{10}$, $10^{11}$, $10^{12}$, $10^{13}$, or $10^{14}$ vgs/mL. In one embodiment, rAAV particles of higher than $10^{13}$ vgs/mL are administered. The rAAV particles can be administered as a single dose, or divided into two or more administrations as may be required to achieve therapy of the particular disease or disorder being treated. In some embodiments, 1 µL to 100 µLs are delivered to a subject. In some embodiments, 10 µL to 1000 µLs are delivered to a subject. In some embodiments, 0.5 mL to 10 mLs are delivered to a subject.

If desired, rAAV particles may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The rAAV particles may thus be delivered along with various other agents as required in the particular instance. Such compositions may be purified from host cells or other biological sources, or alternatively may be chemically synthesized.

In certain circumstances it will be desirable to deliver the rAAV particles in suitably formulated pharmaceutical compositions disclosed herein either subcutaneously, intraocularly, intravitreally, subretinally, parenterally, intravenously, intracerebro-ventricularly, intramuscularly, intrathecally, orally, intraperitoneally, by oral or nasal inhalation, or by direct injection to one or more cells, tissues, or organs by direct injection. In some embodiments, the administration is a route suitable for the eye, such as intraocular, intravitreal, or subretinal administration. The pharmaceutical forms of the rAAV particle compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, intravitreal, subretinal, subcutaneous and intraperitoneal administration. In this connection, a sterile aqueous medium that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Sterile injectable solutions are prepared by incorporating the rAAV particles in the required amount in the appropriate solvent with several of the other ingredients enumerated above, as required, followed by filtered sterilization or another sterilization technique. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The amount of rAAV particle or nucleic acid vector compositions and time of administration of such compositions will be within the purview of the skilled artisan having benefit of the present teachings. It is likely, however, that the administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the rAAV particle compositions, either over a relatively short, or a relatively prolonged period of time, as may be determined by the medical practitioner overseeing the administration of such compositions.

The composition may include rAAV particles, either alone, or in combination with one or more additional active ingredients, which may be obtained from natural or recombinant sources or chemically synthesized.

Toxicity and efficacy of the compositions utilized in methods of the disclosure can be determined by standard pharmaceutical procedures, using either cells in culture or experimental animals to determine the LD50 (the dose lethal to 50% of the population). The dose ratio between toxicity and efficacy the therapeutic index and it can be expressed as the ratio LD50/ED50. Those compositions that exhibit large therapeutic indices are preferred. While those that exhibit toxic side effects may be used, care should be taken to design a delivery system that minimizes the potential damage of such side effects. The dosage of compositions as described herein lies generally within a range that includes an ED50 with little or no toxicity. The dosage may vary within this range depending upon the dosage form employed and the route of administration utilized.

Subjects

Aspects of the disclosure relate to methods for use with a subject, such as human or non-human primate subjects. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. In some embodiments, the subject is a human subject. Other exemplary subjects include domesticated animals such as dogs and cats; livestock such as horses, cattle, pigs, sheep, goats, and chickens; and other animals such as mice, rats, guinea pigs, and hamsters.

In some embodiments, the subject has or is suspected of having a disease that may be treated with gene therapy. In some embodiments, the subject has or is suspected of having an ocular disorders such as a cone monochromacy (e.g., blue cone monochromacy) or cone dichromacy (e.g., protanopia or deuteranopia). Blue cone monochromacy (BCM) is characterized by the absence of L- and M-cone function in the retina due to the loss of functional long wavelength-sensitive and medium wave-length sensitive cones in the retina. BCM may result from mutations in a single red or red-green hybrid opsin gene, mutations in both the red and the green opsin genes, rearrangements of the L and M opsin genes, or deletions within the adjacent LCR (locus control region) on the X chromosome. Subjects with BCM have severe vision impairment, poor visual acuity, nystagmus, and photophobia. Protanopia is caused by the absence of red retinal photoreceptors. Deuteranopia is caused by the absence of green retinal photoreceptors. Subjects with BCM or other ocular disorders can be identified by the skilled practitioner using methods known in art, e.g., by clinical ophthalmological examination, electroretinography (ERG), psychophysical testing (e.g., color vision, dark adaptometry), and/or genetic testing.

In some embodiments, the subject has or is suspected of having one or more of Retinitis pigmentosa (RP), Leber congenital amaurosis (LCA), Age-related macular degeneration (AMD), recessive RP, Dominant retinitis pigmentosa, X-linked retinitis pigmentosa, Incomplete X-linked retinitis pigmentosa, dominant, Dominant Leber congenital amaurosis, Recessive ataxia, posterior column with retinitis pigmentosa, Recessive retinitis pigmentosa with para-arteriolar preservation of the RPE, Retinitis pigmentosa RP12, Usher syndrome, Dominant retinitis pigmentosa with sensorineural deafness, Recessive retinitis punctata albescens, Recessive Alström syndrome, Recessive Bardet-Biedl syndrome, Dominant spinocerebellar ataxia w/macular dystrophy or retinal degeneration, Recessive abetalipoproteinemia, Recessive retinitis pigmentosa with macular degeneration, Recessive Refsum disease (adult form), Recessive Refsum disease (infantile form), Recessive enhanced S-cone syndrome, Retinitis pigmentosa with mental retardation, Retinitis pigmentosa with myopathy, Recessive Newfoundland rod-cone dystrophy, Retinitis pigmentosa sinpigmento, Sector retinitis pigmentosa, Regional retinitis pigmentosa, Senior-Loken syndrome, Joubert syndrome, Stargardt disease (juvenile), Stargardt disease (late onset), Dominant macular dystrophy Stargardt type, Dominant Stargardt-like macular dystrophy, Recessive macular dystrophy, Recessive fundus flavimaculatus, Recessive cone-rod dystrophy, X-linked progressive cone-rod dystrophy, Dominant cone-rod dystrophy, Cone-rod dystrophy, de Grouchy syndrome, Dominant cone dystrophy, X-linked cone dystrophy, Recessive cone dystrophy, Recessive cone dystrophy with supernormal rod electroretinogram, X-linked atrophic macular dystrophy, X-linked retinoschisis, Dominant macular dystrophy, Dominant radial, macular drusen, Dominant macular dystrophy (bull's-eye), Dominant macular dystrophy (butterfly-shaped), Dominant adult vitelliform macular dystrophy, Dominant macular dystrophy (North Carolina type), Dominant retinal-cone dystrophy 1, Dominant macular dystrophy (cystoid), Dominant macular dystrophy (atypical vitelliform), Foveomacular atrophy, Dominant macular dystrophy (Best type), Dominant macular dystrophy (North Carolina-like with progressive), Recessive macular dystrophy (juvenile with hypotrichosis), Recessive foveal hypoplasia and anterior segment dysgenesis, Recessive delayed cone adaptation, Macular dystrophy in blue cone monochromacy, Macular pattern dystrophy with type II diabetes and deafness, Flecked Retina of Kandori, Pattern Dystrophy, Dominant Stickler syndrome, Dominant Marshall syndrome, Dominant vitreoretinal degeneration, Dominant familial exudative vitreoretinopathy, Dominant vitreoretinochoroidopathy, Dominant neovascular inflammatory vitreoretinopathy, Goldmann-Favre syndrome, Recessive achromatopsia, Dominant tritanopia, Recessive rod monochromacy, Congenital red-green deficiency, Deuteranopia, Protanopia, Deuteranomaly, Protanomaly, Recessive Oguchi disease, Dominant macular dystrophy (late onset), Recessive gyrate atrophy, Dominant atrophia greata, Dominant central areolar choroidal dystrophy, X-linked choroideremia, Choroidal atrophy, Central areolar, Central, Peripapillary, Dominant progressive bifocal chorioretinal atrophy, Progresive bifocal Chorioretinal atrophy, Dominant Doyne honeycomb retinal degeneration (Malattia Leventinese), Amelogenesis imperfecta, Recessive Bietti crystalline corneoretinal dystrophy, Dominant hereditary vascular retinopathy with Raynaud phenomenon and migraine, Dominant Wagner disease and erosive vitreoretinopathy, Recessive microphthalmos and retinal disease syndrome, Recessive nanophthalmos, Recessive retardation, spasticity and retinal degeneration, Recessive Bothnia dystrophy, Recessive pseudoxanthoma elasticum, Dominant pseudoxanthoma elasticum, Recessive Batten disease (ceroid-lipofuscinosis) (juvenile), Dominant Alagille syndrome, McKusick-Kaufman syndrome, hypoprebetalipoproteinemia, acanthocytosis, palladial degeneration, Recessive Hallervorden-Spatz syndrome, Dominant Sorsby's fundus dystrophy, Oregon eye disease, Kearns-Sayre syndrome, Retinitis pigmentosa with developmental and neurological abnormalities, Basseb Korenzweig Syndrome, Hurler disease, Sanfilippo disease, Scieie disease, Melanoma associated retinopathy, Sheen retinal dystrophy, Duchenne macular dystrophy, Becker macular dystrophy, Birdshot Retinochoroidopathy, Multiple Evanescent White-dot syndrome, Acute Zonal Occult Outer Retinopathy, Retinal vein occlusion, Retinal artery occlusion, Diabetic retinopathy, Retinal toxicity, Retinal injury, Retinal traumata, Retinal laser lesions, and Fundus Albipunctata.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: AAV-Mediated Gene Therapy Restores M-Cone Function in S-Opsin Only Opn1mw KO Mice Color vision is facilitated by cones expressing different opsin photopigments. Cones containing M- or S-opsin are sensitive to middle or short wavelength visible light, respectively. Opn1mw knock-out (M-opsin KO) mice lack of M-opsin expression while maintaining a normal number of cones and S-opsin expression. Similarly, Blue Cone Monochromacy (BCM) patients lack functioning middle and long wavelength opsins and only express S-opsin. Therefore, the Opn1mw KO mouse is a good model to establish preclinical efficacy and safety data in future BCM gene therapy clinical trial. It was therefore tested whether AAV-mediated M-opsin expression in cones can restore M-cone function/structure in this model.

Figure 1B:
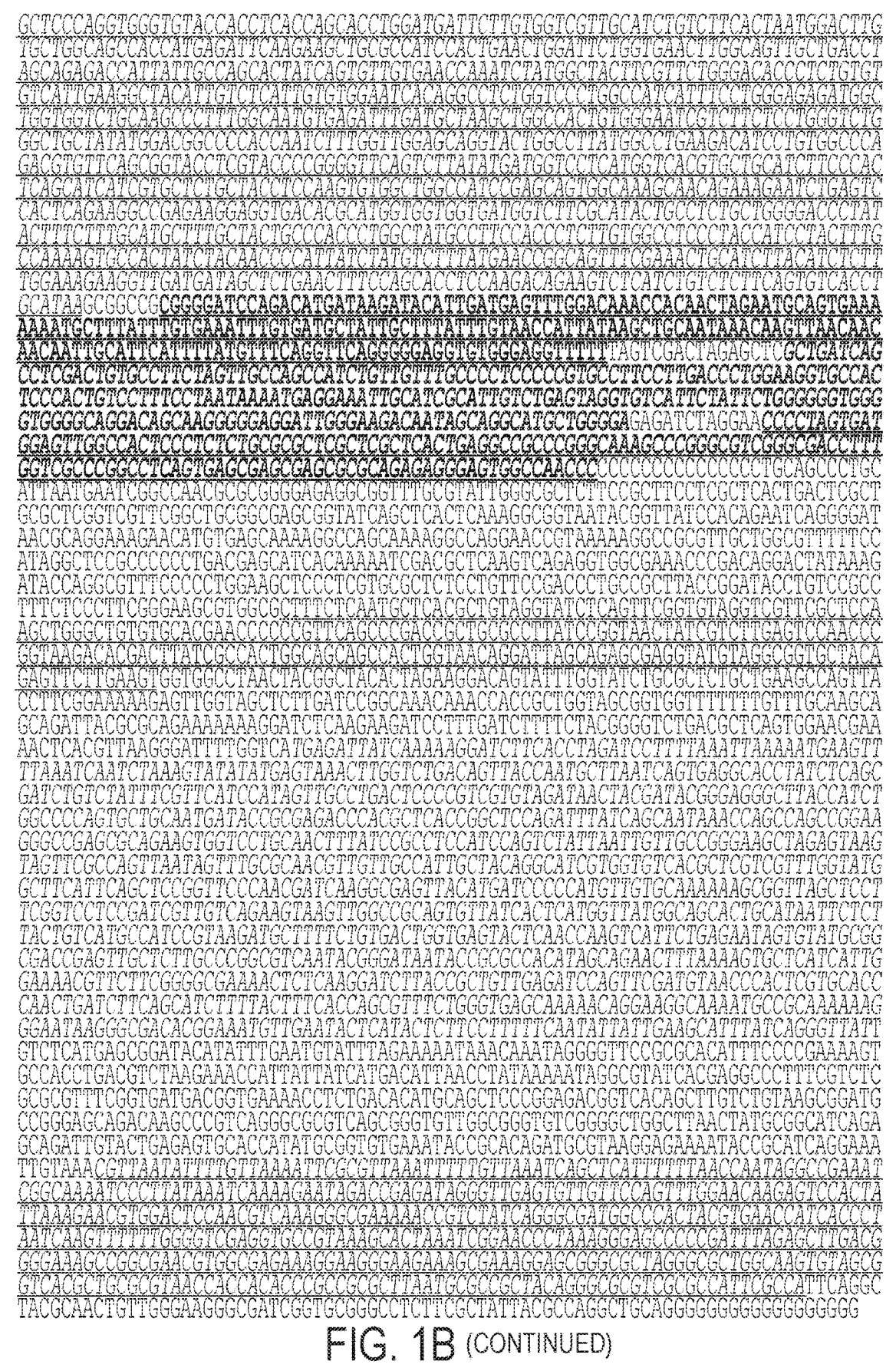

Opn1mw KO mice were generated by inserting a gene trap into intron 2 of the mouse Opn1mw gene. A plasmid containing a PR2.1-M-opsin construct was generated (FIGS. 1A and 1B). The construct contained the mouse cone opsin middle wavelength cDNA driven by the cone-specific PR2.1 promoter. The cDNA was followed by a SV40 polyadenylation signal and a bovine growth hormone polyadenylation signal. The expression cassette was flanked by inverted terminal repeats (ITRs). The expression construct was packaged into AAV5 using standard techniques. At postnatal day 14 (P14), one µl of AAV5-PR2.1-mouse-M-opsin vector ($10^{13}$ vector genome particles/mL) was injected subretinally into one eye of each Opn1mw KO mouse. The other eye was uninjected and served as a control. M-cone mediated ERGs were recorded at two months after injection. Treated and untreated eyes were harvested immediately after ERG recording for immunohistochemical studies.

Figure 2:
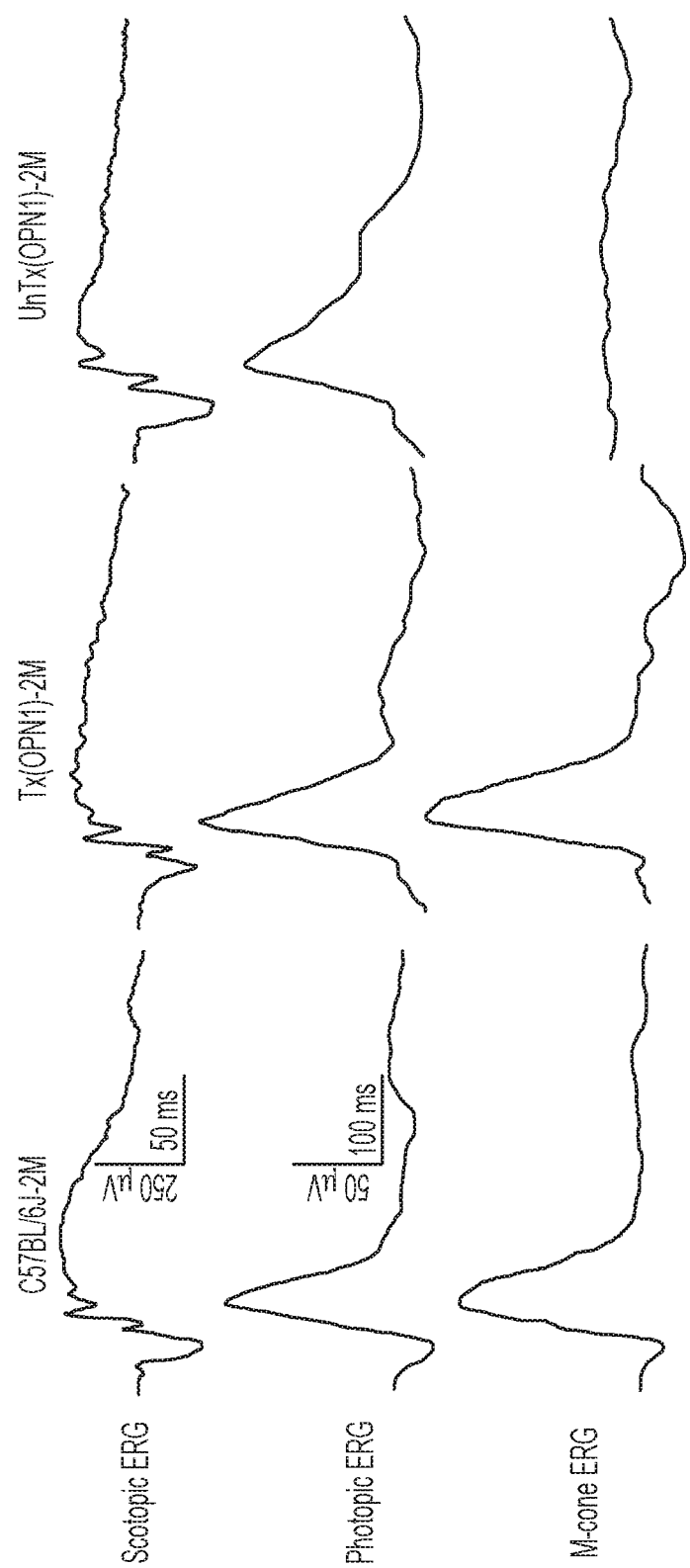
FIG. 2 is a series of traces showing scotopic ERG, photopic ERG, and M-cone ERG in Opn1mw knock-out (KO) mice two months after P14 treatment with AAV5-PR2.1-mouse M-opsin. Tx=treated eye. UnTx=untreated eye. The left-most traces are from wild-type mice and the middle and right-most traces are from Opn1mw KO mice.
Figure 3:
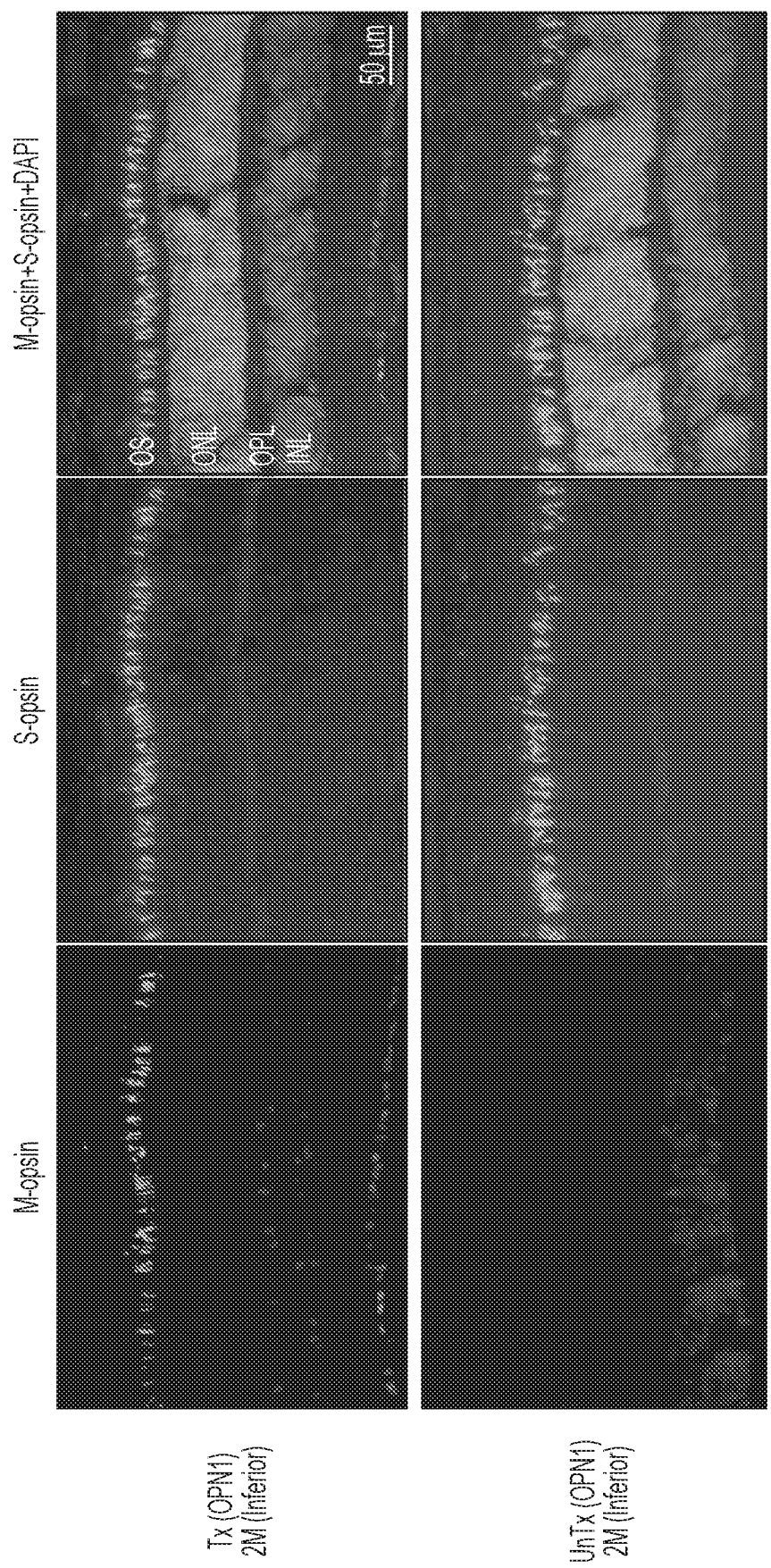
FIG. 3 is a series of photographs showing M-opsin (left column), S-opsin (middle column), or an overlay of M-opsin, S-opsin and DAPI (right column) in the inferior retina of a treated eye (Tx) or untreated eye (UnTx) from Opn1mw knock-out (KO) mice.
Figure 4:
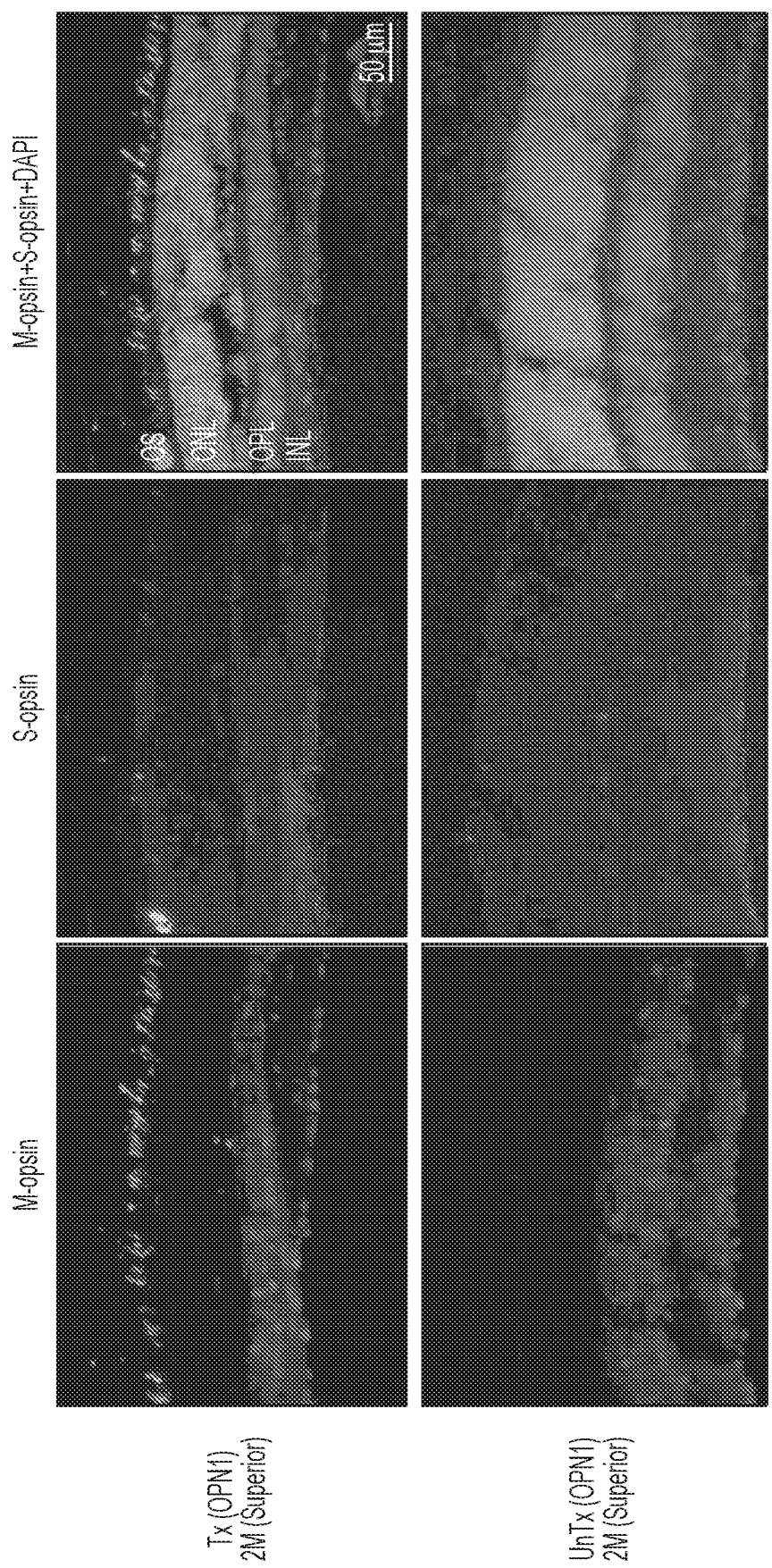
FIG. 4 is a series of photographs showing M-opsin (left column), S-opsin (middle column), or an overlay of M-opsin, S-opsin and DAPI (right column) in the superior retina of a treated eye (Tx) or untreated eye (UnTx) from Opn1mw knock-out (KO) mice.

Two months after treatment, nearly normal dark-adapted rod ERG waveforms were recorded in either treated or untreated Opn1mw KO eyes with a mild reduction of ERG amplitudes in treated eyes, likely due to slight subretinal injection-related damage (FIG. 2). Cone mediated light-adapted ERGs or S-cone mediated ERGs were also recorded from treated and untreated eyes; M-cone mediated ERGs were restored only in treated but not in untreated Opn1mw KO eyes. Cone-opsin staining showed that S-opsin was present in both treated and untreated eyes, mainly in central and inferior retina (FIG. 3, middle column). No M-opsin was evident in untreated eyes (FIG. 3, left column, bottom row). In contrast, abundant M-opsin positive cones were observed in treated eyes throughout the retina (FIG. 3, left column, top row). AAV-mediated M-opsin expression not only co-localized with S-opsin expression in central and inferior cone outer segments, but was also found in the superior retina which has little or no S-opsin (FIG. 4, top row).

Since Opn1mw KO mice express only S-opsin, they serve as a model for human BCM. AAV5-PR2.1-mouse-M-opsin mediated gene therapy restored M-opsin expression and M-opsin function in Opn1mw KO mice. These results serve as a baseline for studying long-term M-cone rescue in Opn1mw KO mice and for developing a BCM gene therapy.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A nucleic acid comprising an expression construct containing an M-opsin gene operably linked to a cone-specific promoter, wherein the expression construct is flanked by inverted terminal repeat sequences, wherein the cone-specific promoter is a PR2.1 promoter having the sequence of SEQ ID NO: 1.

2. The nucleic acid of claim 1, wherein the expression construct further contains nucleic acid segments that encode an SV40 polyadenylation signal and a bovine growth hormone polyadenylation signal, wherein the nucleic acid segments are positioned 3' to the M-opsin gene.

3. A nucleic acid comprising an expression construct containing an M-opsin gene operably linked to a cone-specific promoter, wherein the expression construct is flanked by inverted terminal repeat sequences, wherein the nucleic acid comprises the sequence of SEQ ID NO: 2.

4. The nucleic acid of claim 1, wherein the nucleic acid is a recombinant adeno-associated virus (rAAV) vector.

5. A recombinant adeno-associated virus (rAAV) particle comprising the nucleic acid of claim 4.

6. The rAAV particle of claim 5, wherein the rAAV particle is an AAV5 particle.

7. A composition comprising a plurality of the rAAV particle of claim 5.

8. The composition of claim 7, further comprising a pharmaceutically acceptable carrier.

9. A method of treating a cone monochromacy in a subject, the method comprising:
administering a therapeutically effective amount of the rAAV particle of claim 5 or the composition of claim 7 to a subject having a cone monochromacy.

10. The method of claim 9, wherein the rAAV particle or composition are administered via subretinal injection.

11. The method of claim 9, wherein the subject has blue cone monochromacy.

12. A composition comprising a plurality of the rAAV particle of claim 6.

13. The composition of claim 12, further comprising a pharmaceutically acceptable carrier.

14. A method of treating a cone monochromacy in a subject, the method comprising:
administering a therapeutically effective amount of the rAAV particle of claim 6 or the composition of claim 8 to a subject having a cone monochromacy.

15. The method of claim 14, wherein the rAAV particle or composition are administered via subretinal injection.

16. The method of claim 14, wherein the subject has blue cone monochromacy.

17. The method of claim 15, wherein the subject has blue cone monochromacy.

18. The method of claim 10, wherein the subject has blue cone monochromacy.

* * * * *

SEQUENCE LISTING

<160> NUMBER OF SEQ ID NOS: 9

<210> SEQ ID NO 1

<211> LENGTH: 2109
<212> TYPE: DNA
<213> ORGANISM: Artificial Sequence
<220> FEATURE:
<223> OTHER INFORMATION: Synthetic polynucleotide

<400> SEQUENCE: 1

| | | | | | |
|---|---|---|---|---|---|
| ccccggggga | tcctctagag | tcgacaggcc | tacagcagcc | agggtgagat | tatgaggctg | 60 |
| agctgagaat | atcaagactg | taccgagtag | ggggccttgg | caagtgtgga | gagcccggca | 120 |
| gctggggcag | agggcggagt | acggtgtgcg | tttacggacc | tcttcaaacg | aggtaggaag | 180 |
| gtcagaagtc | aaaaagggaa | caaatgatgt | ttaaccacac | aaaaatgaaa | atccaatggt | 240 |
| tggatatcca | ttccaaatac | acaaaggcaa | cggataagtg | atccgggcca | ggcacagaag | 300 |
| gccatgcacc | cgtaggattg | cactcagagc | tcccaaatgc | ataggaatag | aagggtgggt | 360 |
| gcaggaggct | gaggggtggg | gaaagggcat | gggtgtttca | tgaggacaga | gcttccgttt | 420 |
| catgcaatga | aaagagtttg | gagacggatg | gtggtgactg | gactatacac | ttacacacgg | 480 |
| tagcgatggt | acactttgta | ttatgtatat | tttaccacga | tctttttaaa | gtgtcaaagg | 540 |
| caaatggcca | atggttcct | tgtcctatag | ctgtagcagc | catcggctgt | tagtgacaaa | 600 |
| gcccctgagt | caagatgaca | gcagccccca | taactcctaa | tcggctctcc | cgcgtggagt | 660 |
| catttaggag | tagtcgcatt | agagacaagt | ccaacatcta | atcttccacc | ctgccagggc | 720 |
| cccagctggc | agcgagggtg | ggagactccg | ggcagagcag | agggcgctga | cattggggcc | 780 |
| cggcctggct | tgggtccctc | tggccttttcc | ccaggggccc | tctttccttg | gggctttctt | 840 |
| gggccgccac | tgctcccgct | cctctccccc | catcccaccc | cctcacccccc | tcgttcttca | 900 |
| tatccttctc | tagtgctccc | tccactttca | tccacccttc | tgcaagagtg | tgggaccaca | 960 |
| aatgagtttt | cacctggcct | ggggacacac | gtgcccccac | aggtgctgag | tgactttcta | 1020 |
| ggacagtaat | ctgctttagg | ctaaaatggg | acttgatctt | ctgttagccc | taatcatcaa | 1080 |
| ttagcagagc | cggtgaaggt | gcagaaccta | ccgccttttcc | aggcctcctc | ccacctctgc | 1140 |
| cacctccact | ctccttcctg | gatgtggggg | gctggcacac | gtgtggccca | gggcattggt | 1200 |
| gggattgcac | tgagctgggt | cattagcgta | atcctggaca | agggcagaca | gggcgagcgg | 1260 |
| agggccagct | ccggggctca | ggcaaggctg | ggggcttccc | ccagacaccc | cactcctcct | 1320 |
| ctgctggacc | cccacttcat | agggcacttc | gtgttctcaa | agggcttcca | aatagcatgg | 1380 |
| tggccttgga | tgcccaggga | agcctcagag | ttgcttatct | ccctctagac | agaaggggaa | 1440 |
| tctcggtcaa | gagggagagg | tcgccctgtt | caaggccacc | cagccagctc | atggcggtaa | 1500 |
| tgggacaagg | ctggccagcc | atcccaccct | cagaagggac | ccggtggggc | aggtgatctc | 1560 |
| agaggaggct | cacttctggg | tctcacattc | ttggatccgg | ttccaggcct | cggccctaaa | 1620 |
| tagtctccct | gggctttcaa | gagaaccaca | tgagaaagga | ggattcgggc | tctgagcagt | 1680 |
| ttcaccaccc | acccccagt | ctgcaaatcc | tgacccgagg | gtccacctgc | cccaaaggcg | 1740 |
| gacgcaggac | agtagaaggg | aacagagaac | acataaacac | agagagggcc | acagcggctc | 1800 |
| ccacagtcac | cgccaccttc | ctggcgggga | tgggtggggc | gtctgagttt | ggttcccagc | 1860 |
| aaatccctct | gagccgccct | tgcgggctcg | cctcaggagc | agggagcaa | gaggtgggag | 1920 |
| gaggaggtct | aagtcccagg | cccaattaag | agatcaggta | gtgtagggtt | tgggagcttt | 1980 |
| taaggtgaag | aggccggggc | tgatcccaca | ggccagtata | aagcgccgtg | accctcaggt | 2040 |
| gatgcgccag | ggccggctgc | ctgcggggac | agggcttttcc | atagccatga | ggatccgaat | 2100 |
| tcggatccc | | | | | 2109 |

<210> SEQ ID NO 2
<211> LENGTH: 7029
<212> TYPE: DNA
<213> ORGANISM: Artificial Sequence
<220> FEATURE:
<223> OTHER INFORMATION: Synthetic polynucleotide

<400> SEQUENCE: 2

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctagatc tgaattcggt accccgggg gatcctctag     180
agtcgacagg cctacagcag ccagggtgag attatgaggc tgagctgaga atatcaagac     240
tgtaccgagt aggggccctt ggcaagtgtg gagagcccgg cagctgggc agagggcgga     300
gtacggtgtg cgtttacgga cctcttcaaa cgaggtagga aggtcagaag tcaaaaggg     360
aacaaatgat gtttaaccac acaaaaatga aaatccaatg gttggatatc cattccaaat     420
acacaaaggc aacggataag tgatccgggc caggcacaga aggccatgca cccgtaggat     480
tgcactcaga gctcccaaat gcataggaat agaagggtgg gtgcaggagg ctgaggggtg     540
gggaaagggc atgggtgttt catgaggaca gagcttccgt ttcatgcaat gaaaagagtt     600
tggagacgga tggtggtgac tggactatac acttacacac ggtagcgatg gtacactttg     660
tattatgtat atttttaccac gatctttta aagtgtcaaa ggcaaatggc caaatggttc     720
cttgtcctat agctgtagca gccatcggct gttagtgaca aagcccctga gtcaagatga     780
cagcagcccc cataactcct aatcggctct cccgcgtgga gtcatttagg agtagtcgca     840
ttagagacaa gtccaacatc taatcttcca ccctgccagg gccccagctg gcagcgaggg     900
tgggagactc cgggcagagc agaggcgct gacattgggg cccggcctgg cttgggtccc     960
tctggccttt ccccaggggc cctctttcct tggggctttc ttgggccgcc actgctcccg    1020
ctcctctccc cccatcccac cccctcaccc cctcgttctt catatccttc tctagtgctc    1080
cctccacttt catccaccct tctgcaagag tgtgggacca caaatgagtt ttcacctggc    1140
ctggggacac acgtgccccc acaggtgctg agtgactttc taggacagta atctgctta    1200
ggctaaaatg ggacttgatc ttctgttagc cctaatcatc aattagcaga gccggtgaag    1260
gtgcagaacc taccgccttt ccaggcctcc tcccacctct gccacctcca ctctccttcc    1320
tgggatgtgg gggctggcac acgtgtggcc cagggcattg gtgggattgc actgagctgg    1380
gtcattagcg taatcctgga caagggcaga cagggcgagc ggagggccag ctccggggct    1440
caggcaaggc tgggggcttc ccccagacac cccactcctc ctctgctgga cccccacttc    1500
atagggcact tcgtgttctc aaagggcttc caaatagcat ggtggccttg gatgcccagg    1560
gaagcctcag agttgcttat ctccctctag acagaagggg aatctcggtc aagagggaga    1620
ggtcgccctg ttcaaggcca cccagccagc tcatggcggt aatgggacaa ggctggccag    1680
ccatcccacc ctcagaaggg acccggtggg gcaggtgatc tcagaggagg ctcacttctg    1740
ggtctcacat tcttggatcc ggttccaggc ctcggcccta aatagtctcc ctgggctttc    1800
aagagaacca catgagaaag gaggattcgg gctctgagca gtttcaccac ccaccccca    1860
gtctgcaaat cctgacccga ggtccacct gccccaaagg cggacgcagg acagtagaag    1920
ggaacagaga acacataaac acagagaggg ccacagcggc tcccacagtc accgccacct    1980
tcctggcggg gatgggtggg gcgtctgagt ttggttccca gcaaatccct ctgagccgcc    2040
```

```
cttgcgggct cgcctcagga gcaggggagc aagaggtggg aggaggaggt ctaagtccca    2100
ggcccaatta agagatcagg tagtgtaggg tttgggagct tttaaggtga agaggcccgg    2160
gctgatccca caggccagta taaagcgccg tgaccctcag gtgatgcgcc agggccggct    2220
gcctgcgggg acagggcttt ccatagccat gaggatccga attcggatcc ccatgtctag    2280
aggatccggt actcgaggaa ctgaaaaacc agaaagttaa ctggtaagtt tagtctttttt    2340
gtcttttatt tcaggtcccg gatccggtgg tggtgcaaat caaagaactg ctcctcagtg    2400
gatgttgcct ttacttctag gcctgtacgg aagtgttact tctgctctaa aagctgcgga    2460
attgtacccg cggccgccac catggcccaa aggcttacag gtgaacagac actggaccac    2520
tatgaggata gcacccatgc aagcatcttc acctatacca acagcaacag caccaaaggt    2580
ccctttgaag gccccaatta tcacattgct cccaggtggg tgtaccacct caccagcacc    2640
tggatgattc ttgtggtcgt tgcatctgtc ttcactaatg acttgtgct ggcagccacc    2700
atgagattca agaagctgcg ccatccactg aactggattc tggtgaactt ggcagttgct    2760
gacctagcag agaccattat tgccagcact atcagtgttg tgaaccaaat ctatggctac    2820
ttcgttctgg acaccctct gtgtgtcatt gaaggctaca ttgtctcatt gtgtggaatc    2880
acaggcctct ggtccctggc catcatttcc tgggagagat ggctggtggt ctgcaagccc    2940
tttggcaatg tgagatttga tgctaagctg gccactgtgg gaatcgtctt ctcctgggtc    3000
tgggctgcta tatggacggc cccaccaatc tttggttgga gcaggtactg gccttatggc    3060
ctgaagacat cctgtggccc agacgtgttc agcggtacct cgtaccccgg ggttcagtct    3120
tatatgatgg tcctcatggt cacgtgctgc atcttcccac tcagcatcat cgtgctctgc    3180
tacctccaag tgtggctggc catccgagca gtggcaaagc aacagaaaga atctgagtcc    3240
actcagaagg ccgagaagga ggtgacacgc atggtggtgg tgatggtctt cgcatactgc    3300
ctctgctggg accctatac tttctttgca tgctttgcta ctgcccaccc tggctatgcc    3360
ttccaccctc ttgtggcctc cctaccatcc tactttgcca aaagtgccac tatctacaac    3420
cccattatct atgtctttat gaaccggcag tttcgaaact gcatcttaca tctctttgga    3480
aagaaggttg atgatagctc tgaacttttcc agcacctcca agacagaagt ctcatctgtc    3540
tcttcagtgt cacctgcata agcggccgcg gggatccaga catgataaga tacattgatg    3600
agtttggaca aaccacaact agaatgcagt gaaaaaaatg ctttatttgt gaaatttgtg    3660
atgctattgc tttatttgta accattataa gctgcaataa acaagttaac aacaacaatt    3720
gcattcattt tatgtttcag gttcaggggg aggtgtggga ggttttttag tcgactagag    3780
ctcgctgatc agcctcgact gtgccttcta gttgccagcc atctgttgtt tgcccctccc    3840
ccgtgccttc cttgaccctg gaaggtgcca ctcccactgt cctttcctaa taaaatgagg    3900
aaattgcatc gcattgtctg agtaggtgtc attctattct ggggggtggg gtggggcagg    3960
acagcaaggg ggaggattgg gaagacaata gcaggcatgc tggggagaga tctaggaacc    4020
cctagtgatg gagttggcca ctccctctct gcgcgctcgc tcgctcactg aggccgcccg    4080
ggcaaagccc gggcgtcggg cgacctttgg tcgcccggcc tcagtgagcg agcgagcgcg    4140
cagagaggga gtgccaacc ccccccccccc cccccctgca gccctgcatt aatgaatcgg    4200
ccaacgcgcg gggagaggcg gtttgcgtat tgggcgctct tccgcttcct cgctcactga    4260
ctcgctgcgc tcggtcgttc ggctgcggcg agcggtatca gctcactcaa aggcggtaat    4320
acggttatcc acagaatcag gggataacgc aggaaagaac atgtgagcaa aaggccagca    4380
aaaggccagg aaccgtaaaa aggccgcgtt gctggcgttt ttccataggc tccgcccccc    4440
```

```
tgacgagcat cacaaaaatc gacgctcaag tcagaggtgg cgaaacccga caggactata    4500
aagataccag gcgtttcccc ctggaagctc cctcgtgcgc tctcctgttc cgaccctgcc    4560
gcttaccgga tacctgtccg cctttctccc ttcgggaagc gtggcgcttt ctcaatgctc    4620
acgctgtagg tatctcagtt cggtgtaggt cgttcgctcc aagctgggct gtgtgcacga    4680
accccccgtt cagcccgacc gctgcgcctt atccggtaac tatcgtcttg agtccaaccc    4740
ggtaagacac gacttatcgc cactggcagc agccactggt aacaggatta gcagagcgag    4800
gtatgtaggc ggtgctacag agttcttgaa gtggtggcct aactacggct acactagaag    4860
gacagtattt ggtatctgcg ctctgctgaa gccagttacc ttcggaaaaa gagttggtag    4920
ctcttgatcc ggcaaacaaa ccaccgctgg tagcggtggt ttttttgttt gcaagcagca    4980
gattacgcgc agaaaaaaag gatctcaaga agatcctttg atcttttcta cggggtctga    5040
cgctcagtgg aacgaaaact cacgttaagg gattttggtc atgagattat caaaaaggat    5100
cttcacctag atccttttaa attaaaaatg aagttttaaa tcaatctaaa gtatatatga    5160
gtaaacttgg tctgacagtt accaatgctt aatcagtgag gcacctatct cagcgatctg    5220
tctatttcgt tcatccatag ttgcctgact ccccgtcgtg tagataacta cgatacggga    5280
gggcttacca tctggcccca gtgctgcaat gataccgcga cccacgctca ccggctcc     5340 agatttatca gcaataaacc agccagccgg aagggccgag cgcagaagtg gtcctgcaac    5400
tttatccgcc tccatccagt ctattaattg ttgccgggaa gctagagtaa gtagttcgcc    5460
agttaatagt ttgcgcaacg ttgttgccat tgctacaggc atcgtggtgt cacgctcgtc    5520
gtttggtatg gcttcattca gctccggttc ccaacgatca aggcgagtta catgatcccc    5580
catgttgtgc aaaaaagcgg ttagctcctt cggtcctccg atcgttgtca gaagtaagtt    5640
ggccgcagtg ttatcactca tggttatggc agcactgcat aattctctta ctgtcatgcc    5700
atccgtaaga tgcttttctg tgactggtga gtactcaacc aagtcattct gagaatagtg    5760
tatgcggcga ccgagttgct cttgcccggc gtcaatacgg gataataccg cgccacatag    5820
cagaacttta aaagtgctca tcattggaaa acgttcttcg gggcgaaaac tctcaaggat    5880
cttaccgctg ttgagatcca gttcgatgta acccactcgt gcacccaact gatcttcagc    5940
atcttttact ttcaccagcg tttctgggtg agcaaaaaca ggaaggcaaa atgccgcaaa    6000
aaagggaata agggcgacac ggaaatgttg aatactcata ctcttccttt ttcaatatta    6060
ttgaagcatt tatcagggtt attgtctcat gagcggatac atatttgaat gtatttagaa    6120
aaataaacaa ataggggttc cgcgcacatt tccccgaaaa gtgccacctg acgtctaaga    6180
aaccattatt atcatgacat taacctataa aaataggcgt atcacgaggc cctttcgtct    6240
cgcgcgtttc ggtgatgacg gtgaaaacct ctgacacatg cagctcccgg agacggtcac    6300
agcttgtctg taagcggatg ccgggagcag acaagcccgt cagggcgcgt cagcgggtgt    6360
tggcgggtgt cggggctggc ttaactatgc ggcatcagag cagattgtac tgagagtgca    6420
ccatatgcgg tgtgaaatac cgcacagatg cgtaaggaga aaataccgca tcaggaaatt    6480
gtaaacgtta atattttgtt aaaattcgcg ttaaattttt gttaaatcag ctcatttttt    6540
aaccaatagg ccgaaatcgg caaaatccct tataaatcaa agaatagac cgagataggg     6600 ttgagtgttg ttccagtttg gaacaagagt ccactattaa agaacgtgga ctccaacgtc    6660
aaagggcgaa aaaccgtcta tcagggcgat ggcccactac gtgaaccatc acctaatca    6720 agttttttgg ggtcgaggtg ccgtaaagca ctaaatcgga accctaaagg gagcccccga    6780
```

| | |
|---|---|
| tttagagctt gacggggaaa gccggcgaac gtggcgagaa aggaagggaa gaaagcgaaa | 6840 |
| ggagcgggcg ctagggcgct ggcaagtgta gcggtcacgc tgcgcgtaac caccacaccc | 6900 |
| gccgcgctta atgcgccgct acagggcgcg tcgcgccatt cgccattcag gctacgcaac | 6960 |
| tgttgggaag ggcgatcggt gcgggcctct tcgctattac gccaggctgc agggggggg | 7020 |
| gggggggg | 7029 |

```
<210> SEQ ID NO 3
<211> LENGTH: 1101
<212> TYPE: DNA
<213> ORGANISM: Mus musculus

<400> SEQUENCE: 3
```

| | |
|---|---|
| cagagacagt tttctacagc catggcccaa aggcttacag gtgaacagac actggaccac | 60 |
| tatgaggata gcacccatgc aagcatcttc acctatacca acagcaacag caccaaaggt | 120 |
| cccttttgaag gccccaatta tcacattgct cccaggtggg tgtaccacct caccagcacc | 180 |
| tggatgattc ttgtggtcgt tgcatctgtc ttcactaatg acttgtgct ggcagccacc | 240 |
| atgagattca agaagctgcg ccatccactg aactggattc tggtgaactt ggcagttgct | 300 |
| gacctagcag agaccattat tgccagcact atcagtgttg taaccaaat ctatggctac | 360 |
| ttcgttctgg acaccctct gtgtgtcatt gaaggctaca ttgtctcatt gtgtggaatc | 420 |
| acaggcctct ggtccctggc catcattcc tgggagagat ggctggtggt ctgcaagccc | 480 |
| tttggcaatg tgagatttga tgctaagctg gccactgtgg aatcgtctt ctcctgggtc | 540 |
| tgggctgcta tatggacggc cccaccaatc tttggttgga gcaggtactg gccttatggc | 600 |
| ctgaagacat cctgtggccc agacgtgttc agcggtacct cgtaccccgg ggttcagtct | 660 |
| tatatgatgg tcctcatggt cacgtgctgc atcttccac tcagcatcat cgtgctctgc | 720 |
| tacctccaag tgtggctggc catccgagca gtggcaaagc aacagaaaga atctgagtcc | 780 |
| actcagaagg ccgagaagga ggtgacacgc atggtggtgg tgatggtctt cgcatactgc | 840 |
| ctctgctggg acccctatac tttctttgca tgctttgcta ctgcccaccc tggctatgcc | 900 |
| ttccacccctc ttgtggcctc cctaccatcc tactttgcca aaagtgccac tatctacaac | 960 |
| cccattatct atgtctttat gaaccggcag tttcgaaact gcatcttaca tctctttgga | 1020 |
| aagaaggttg atgatagctc tgaactttcc agcacctcca agacagaagt ctcatctgtc | 1080 |
| tcttcagtgt caacctgcata a | 1101 |

```
<210> SEQ ID NO 4
<211> LENGTH: 1095
<212> TYPE: DNA
<213> ORGANISM: Homo sapiens

<400> SEQUENCE: 4
```

| | |
|---|---|
| atggcccagc agtggagcct ccaaaggctc gcaggccgcc atccgcagga cagctatgag | 60 |
| gacagcaccc agtccagcat cttcacctac accaacagca ctccaccag aggccccttc | 120 |
| gaaggcccga attaccacat cgctcccaga tgggtgtacc acctcaccag tgtctggatg | 180 |
| atctttgtgg tcattgcatc cgtcttcaca aatgggcttg tgctggcggc caccatgaag | 240 |
| ttcaagaagc tgcgccaccc gctgaactgg atcctggtga acctggcggt cgctgacctg | 300 |
| gcagagaccg tcatcgccag cactatcagc gttgtgaacc aggtctatgg ctacttcgtg | 360 |
| ctgggccacc ctatgtgtgt cctggagggc tacaccgtct ccctgtgtgg gatcacaggt | 420 |
| ctctggtctc tggccatcat ttcctgggag agatggatgg tggtctgcaa gcccttggc | 480 |

```
aatgtgagat tgatgccaa gctggccatc gtgggcattg tcttctcctg gatctggtct    540
gctgtgtgga cagccccgcc catctttggt tggagcaggt actggcccca cggcctgaag    600
acttcatgcg gcccagacgt gttcagcggc agctcgtacc ccggggtgca gtcttacatg    660
attgtcctca tggtcacctg ctgcatcacc ccactcagca tcatcgtgct ctgctacctc    720
caagtgtggc tggccatccg agcggtggca aagcagcaga aagagtctga atccacccag    780
aaggcagaga aggaagtgac gcgcatggtg gtggtgatgg tcctggcatt ctgcttctgc    840
tggggaccat acgccttctt cgcatgcttt gctgctgcca accctggcta ccccttccac    900
cctttgatgg ctgccctgcc ggccttcttt gccaaaagtg ccactatcta aacccccgtt    960
atctatgtct ttatgaaccg gcagtttcga aactgcatct tgcagctttt cgggaagaag   1020
gttgacgatg gctctgaact ctccagcgcc tccaaaacgg aggtctcatc tgtgtcctcg   1080
gtatcgcctg catga                                                    1095
```

<210> SEQ ID NO 5
<211> LENGTH: 359
<212> TYPE: PRT
<213> ORGANISM: Mus musculus

<400> SEQUENCE: 5

```
Met Ala Gln Arg Leu Thr Gly Glu Gln Thr Leu Asp His Tyr Glu Asp
1               5                  10                  15

Ser Thr His Ala Ser Ile Phe Thr Tyr Thr Asn Ser Asn Ser Thr Lys
            20                  25                  30

Gly Pro Phe Glu Gly Pro Asn Tyr His Ile Ala Pro Arg Trp Val Tyr
        35                  40                  45

His Leu Thr Ser Thr Trp Met Ile Leu Val Val Val Ala Ser Val Phe
    50                  55                  60

Thr Asn Gly Leu Val Leu Ala Ala Thr Met Arg Phe Lys Lys Leu Arg
65                  70                  75                  80

His Pro Leu Asn Trp Ile Leu Val Asn Leu Ala Val Ala Asp Leu Ala
                85                  90                  95

Glu Thr Ile Ile Ala Ser Thr Ile Ser Val Val Asn Gln Ile Tyr Gly
            100                 105                 110

Tyr Phe Val Leu Gly His Pro Leu Cys Val Ile Glu Gly Tyr Ile Val
        115                 120                 125

Ser Leu Cys Gly Ile Thr Gly Leu Trp Ser Leu Ala Ile Ile Ser Trp
    130                 135                 140

Glu Arg Trp Leu Val Val Cys Lys Pro Phe Gly Asn Val Arg Phe Asp
145                 150                 155                 160

Ala Lys Leu Ala Thr Val Gly Ile Val Phe Ser Trp Val Trp Ala Ala
                165                 170                 175

Ile Trp Thr Ala Pro Pro Ile Phe Gly Trp Ser Arg Tyr Trp Pro Tyr
            180                 185                 190

Gly Leu Lys Thr Ser Cys Gly Pro Asp Val Phe Ser Gly Thr Ser Tyr
        195                 200                 205

Pro Gly Val Gln Ser Tyr Met Met Val Leu Met Val Thr Cys Cys Ile
    210                 215                 220

Phe Pro Leu Ser Ile Ile Val Leu Cys Tyr Leu Gln Val Trp Leu Ala
225                 230                 235                 240

Ile Arg Ala Val Ala Lys Gln Gln Lys Glu Ser Glu Ser Thr Gln Lys
                245                 250                 255
```

Ala Glu Lys Glu Val Thr Arg Met Val Val Met Val Phe Ala Tyr
            260                 265                 270

Cys Leu Cys Trp Gly Pro Tyr Thr Phe Phe Ala Cys Phe Ala Thr Ala
        275                 280                 285

His Pro Gly Tyr Ala Phe His Pro Leu Val Ala Ser Leu Pro Ser Tyr
    290                 295                 300

Phe Ala Lys Ser Ala Thr Ile Tyr Asn Pro Ile Ile Tyr Val Phe Met
305                 310                 315                 320

Asn Arg Gln Phe Arg Asn Cys Ile Leu His Leu Phe Gly Lys Lys Val
                325                 330                 335

Asp Asp Ser Ser Glu Leu Ser Ser Thr Ser Lys Thr Glu Val Ser Ser
            340                 345                 350

Val Ser Ser Val Ser Pro Ala
            355

<210> SEQ ID NO 6
<211> LENGTH: 364
<212> TYPE: PRT
<213> ORGANISM: Homo sapiens

<400> SEQUENCE: 6

Met Ala Gln Gln Trp Ser Leu Gln Arg Leu Ala Gly Arg His Pro Gln
1               5                   10                  15

Asp Ser Tyr Glu Asp Ser Thr Gln Ser Ser Ile Phe Thr Tyr Thr Asn
            20                  25                  30

Ser Asn Ser Thr Arg Gly Pro Phe Glu Gly Pro Asn Tyr His Ile Ala
        35                  40                  45

Pro Arg Trp Val Tyr His Leu Thr Ser Val Trp Met Ile Phe Val Val
    50                  55                  60

Ile Ala Ser Val Phe Thr Asn Gly Leu Val Leu Ala Ala Thr Met Lys
65                  70                  75                  80

Phe Lys Lys Leu Arg His Pro Leu Asn Trp Ile Leu Val Asn Leu Ala
                85                  90                  95

Val Ala Asp Leu Ala Glu Thr Val Ile Ala Ser Thr Ile Ser Val Val
            100                 105                 110

Asn Gln Val Tyr Gly Tyr Phe Val Leu Gly His Pro Met Cys Val Leu
        115                 120                 125

Glu Gly Tyr Thr Val Ser Leu Cys Gly Ile Thr Gly Leu Trp Ser Leu
    130                 135                 140

Ala Ile Ile Ser Trp Glu Arg Trp Met Val Val Cys Lys Pro Phe Gly
145                 150                 155                 160

Asn Val Arg Phe Asp Ala Lys Leu Ala Ile Val Gly Ile Val Phe Ser
                165                 170                 175

Trp Ile Trp Ser Ala Val Trp Thr Ala Pro Pro Ile Phe Gly Trp Ser
            180                 185                 190

Arg Tyr Trp Pro His Gly Leu Lys Thr Ser Cys Gly Pro Asp Val Phe
        195                 200                 205

Ser Gly Ser Ser Tyr Pro Gly Val Gln Ser Tyr Met Ile Val Leu Met
    210                 215                 220

Val Thr Cys Cys Ile Thr Pro Leu Ser Ile Ile Val Leu Cys Tyr Leu
225                 230                 235                 240

Gln Val Trp Leu Ala Ile Arg Ala Val Ala Lys Gln Gln Lys Glu Ser
                245                 250                 255

Glu Ser Thr Gln Lys Ala Glu Lys Glu Val Thr Arg Met Val Val Val
            260                 265                 270

```
Met Val Leu Ala Phe Cys Phe Cys Trp Gly Pro Tyr Ala Phe Phe Ala
            275                 280                 285

Cys Phe Ala Ala Ala Asn Pro Gly Tyr Pro Phe His Pro Leu Met Ala
290                 295                 300

Ala Leu Pro Ala Phe Phe Ala Lys Ser Ala Thr Ile Tyr Asn Pro Val
305                 310                 315                 320

Ile Tyr Val Phe Met Asn Arg Gln Phe Arg Asn Cys Ile Leu Gln Leu
                325                 330                 335

Phe Gly Lys Lys Val Asp Asp Gly Ser Glu Leu Ser Ser Ala Ser Lys
            340                 345                 350

Thr Glu Val Ser Ser Val Ser Ser Val Ser Pro Ala
            355                 360

<210> SEQ ID NO 7
<211> LENGTH: 199
<212> TYPE: DNA
<213> ORGANISM: Artificial Sequence
<220> FEATURE:
<223> OTHER INFORMATION: Synthetic polynucleotide

<400> SEQUENCE: 7
cggggatcca gacatgataa gatacattga tgagtttgga caaaccacaa ctagaatgca      60
gtgaaaaaaa tgctttattt gtgaaatttg tgatgctatt gctttatttg taaccattat     120
aagctgcaat aaacaagtta acaacaacaa ttgcattcat tttatgtttc aggttcaggg     180
ggaggtgtgg gaggtttt                                                   199

<210> SEQ ID NO 8
<211> LENGTH: 223
<212> TYPE: DNA
<213> ORGANISM: Artificial Sequence
<220> FEATURE:
<223> OTHER INFORMATION: Synthetic polynucleotide

<400> SEQUENCE: 8
gctgatcagc ctcgactgtg ccttctagtt gccagccatc tgttgtttgc ccctcccccg      60
tgccttcctt gaccctggaa ggtgccactc ccactgtcct ttcctaataa aatgaggaaa     120
ttgcatcgca ttgtctgagt aggtgtcatt ctattctggg gggtggggtg gggcaggaca     180
gcaaggggga ggattgggaa gacaatagca ggcatgctgg gga                       223

<210> SEQ ID NO 9
<211> LENGTH: 724
<212> TYPE: PRT
<213> ORGANISM: Homo sapiens

<400> SEQUENCE: 9

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
```

```
                    85                  90                  95
Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
            115                 120                 125

Gly Leu Val Glu Glu Gly Ala Lys Thr Ala Pro Thr Gly Lys Arg Ile
            130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
            165                 170                 175

Gln Leu Gln Ile Pro Ala Gln Pro Ala Ser Leu Gly Ala Asp Thr
            180                 185                 190

Met Ser Ala Gly Gly Gly Pro Leu Gly Asp Asn Gln Gly Ala
            195                 200                 205

Asp Gly Val Gly Asn Ala Ser Gly Asp Trp His Cys Asp Ser Thr Trp
            210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
            245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
            275                 280                 285

Arg Leu Ile Asn Asn Tyr Trp Gly Phe Arg Pro Arg Ser Leu Arg Val
            290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
            325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
            355                 360                 365

Ala Thr Leu Asn Arg Asp Asn Thr Glu Asn Pro Thr Glu Arg Ser Ser
            370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
            405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Thr Gly Gly Val Gln
            435                 440                 445

Phe Asn Lys Asn Leu Ala Gly Arg Tyr Ala Asn Thr Tyr Lys Asn Trp
            450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
            485                 490                 495

Leu Glu Gly Ala Ser Tyr Gln Val Pro Pro Gln Pro Asn Gly Met Thr
            500                 505                 510
```

```
Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
        610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
        690                 695                 700

Ser Thr Gly Glu Tyr Arg Thr Thr Arg Pro Ile Gly Thr Arg Tyr Leu
705                 710                 715                 720

Thr Arg Pro Leu
```